(12) United States Patent
Charbonniere et al.

(10) Patent No.: US 7,838,299 B2
(45) Date of Patent: Nov. 23, 2010

(54) LANTHANIDE COMPLEXES, PREPARATION AND USES THEREOF

(75) Inventors: Loïc Charbonniere, Weyersheim (FR); Raymond Ziessel, Souffelweysheim (FR); Nicolas Weibel, Colmar (FR); Aldo Roda, Bologna (IT); Massimo Guardigli, Roncalceci (IT)

(73) Assignees: Centre National de la Recherche Scientifique, Paris (FR); Universite Louis Pasteur de Strasbourg, Strasbourg (FR)

( * ) Notice: Subject to any disclaimer, the term of this patent is extended or adjusted under 35 U.S.C. 154(b) by 0 days.

(21) Appl. No.: 12/714,357

(22) Filed: Feb. 26, 2010

(65) Prior Publication Data
US 2010/0216252 A1   Aug. 26, 2010

Related U.S. Application Data

(62) Division of application No. 10/565,804, filed on Jan. 25, 2006, now Pat. No. 7,709,263.

(51) Int. Cl.
*G01N 33/20* (2006.01)
(52) U.S. Cl. ................ 436/82; 436/172; 534/10; 534/15; 534/16; 546/256
(58) Field of Classification Search ............ 436/82, 436/172; 534/10, 15, 16; 546/256
See application file for complete search history.

(56) References Cited

U.S. PATENT DOCUMENTS 5,216,134 A   6/1993   Mukkala et al.
5,559,214 A   9/1996   Delecki et al.
5,892,029 A   4/1999   Raymond et al.
6,509,324 B1  1/2003   Franzini et al.
2002/0090342 A1  7/2002  Liu

FOREIGN PATENT DOCUMENTS

| EP | 0493745 A1 | 7/1991 |
| EP | 0649020 A1 | 4/1995 |
| EP | 0770610 A1 | 5/1997 |
| WO | 02/059097 A1 | 8/2002 |

OTHER PUBLICATIONS

Weibel, Nicolas, et al., "Engineering of Highly Luminescent Lanthanide Tags Suitable for Protein Labeling and Time-Resolved Luminescence Imaging", *J. Am. Chem. Soc.* 126(15):4888-4896 (2004).
Search report from PCT/FR2004/001921, dated Feb. 2, 2005.

*Primary Examiner*—Michael A Marcheschi
*Assistant Examiner*—Jameson Q Ma
(74) *Attorney, Agent, or Firm*—Merchant & Gould

(57) ABSTRACT

The invention relates to compounds, to the complexes they form with a lanthanide, and to the use of the complexes for fluorescence marking or NMR imaging. The complex consists of an Ln ion and a ligand $R^2$—$C(X—R^1)(R^3)$—$NR^4R^5$. $R^1$ is a functional group, X is a single bond or a hydrocarbon-based chain consisting of at least one alkylene or alkenylene group optionally comprising at least one hetero atom or an arylene. $R^2$ is an anionic group $A^2$ or a $C_1$-$C_4$ alkylene or alkenylene group bearing at least one such group $A^2$ and optionally comprising at least one hetero atom. $R^3$ is H or a $C_1$-$C_5$ alkylene or alkenylene group optionally containing at least one hetero atom, and optionally bearing at least one anionic group $A^3$. $R^4$ is a substituent with light-absorbing properties that forms chelate rings with Ln. $R^5$ is a substituent that forms chelate rings with Ln.

15 Claims, 1 Drawing Sheet

LANTHANIDE COMPLEXES, PREPARATION AND USES THEREOF

The present application is a divisional of U.S. patent application Ser. No. 10/565,804, filed Jan. 25, 2006, now U.S. Pat. No. 7,709,263, the contents of which are incorporated herein in their entirety by reference.

BACKGROUND OF THE INVENTION

1. Field of the Invention

The present invention relates to compounds capable of forming complexes with lanthanides, to the complexes obtained and to the uses thereof.

2. Description of the Related Art

The present invention relates to compounds capable of forming complexes with lanthanides, to the complexes obtained and to the uses thereof.

Radioactive markers have been widely used in the field of medical imaging and immunology. On account of the drawbacks of these markers, they have largely been replaced with fluorescent markers.

However, the use of fluorescent markers presents a number of drawbacks, especially due to the auto-fluorescence of the biological media studied and to the scattering of light in the machines. Lanthanide ion complexes have been proposed to allow a time-resolved acquisition that eliminates these drawbacks. In order to be used as a time-resolved luminescent marker, a lanthanide ion complex must have numerous characteristics, the most important of which are hydrophilicity, stability in water, the presence of chromophores capable of generating the antenna effect (Sabbatini, N. et al. Coord. Chem. Rev. 1990, 123, 201), good photophysical properties (high absorption, excitation over a readily accessible energy range, long lifetime of the excited state and high luminescence quantum yield) and a reactive function that allows covalent grafting.

The compounds currently proposed rarely combine all of these criteria. For example, the first complexes developed by the company Wallac Oy under the name Delfia Chelate (Hemmilä, I. et al. Anal. Biochem. 1984, 137, 335) do not have good photophysical properties and it is necessary to perform a lanthanide extraction step in order to measure its luminescence. The compounds developed by CIS Bio International are cryptates, which require the use of fluoride anions in order to increase the luminescence (Hemmilä, I. et al. Drug Discovery Today, 1997, 2, 373). The stability of the compounds also poses serious problems. Thus, the compounds developed by CyberFluor under the name BCPDA only form stable luminescent complexes at high concentrations (Marriott, G. et al., Biophysical Journal, 1994, 67, 957).

Lanthanide complexes, especially of gadolinium, have been used as relaxation agents or contrast agents for NMR medical imaging (Caravan, P. et al. Chem. Rev. 1999, 99, 2293). This use is permitted due to the fact that the first coordination sphere of the lanthanide is not fully saturated with the ligand in aqueous solution, water molecules thus being able to complete the coordination sphere.

SUMMARY OF THE INVENTION

The aim of the present invention is to propose lanthanide complexes that have improved properties over the lanthanide complexes of the prior art. Accordingly, one subject of the invention is novel compounds, their use for preparing complexes with lanthanide ions, and also the use of the complexes obtained as fluorescent markers, and as relaxation agents for NMR or for NMR imaging.

DETAILED DESCRIPTION

Figure 1:
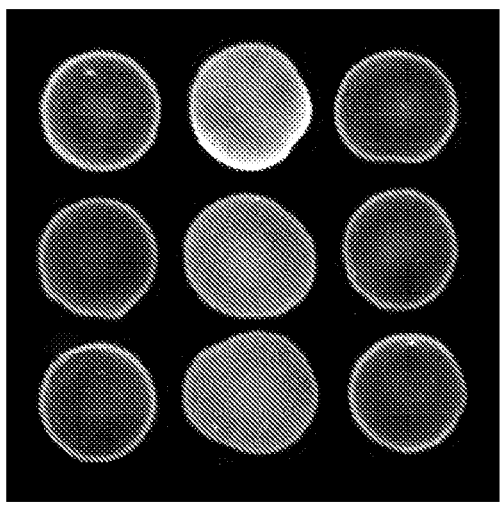
FIG. 1 shows droplets about 750 microns in diameter containing BSA marked with compound 9 (left-hand and right-hand columns on each image) and a fluorescein-marked antibody (middle column on each image) serving as reference (fluorescein-marked rabbit immunoglobulin produced by Dako-Immunoglobuline under the product code F-123). The image on the left was obtained by conventional fluorescence microscopy and the image on the right was obtained by time-resolved luminescence microscopy.
Figure 1:
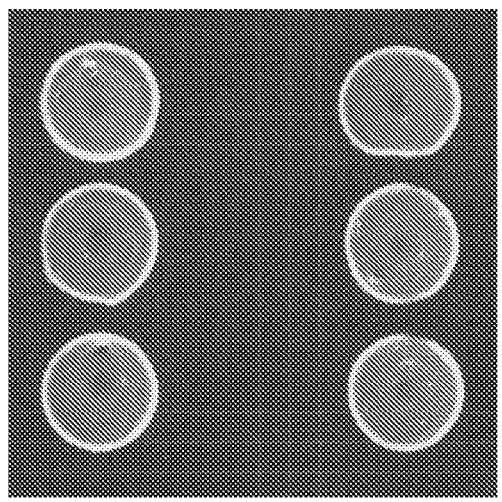

A compound according to the present invention corresponds to formula (I)

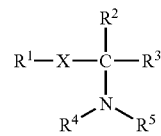

in which
- $R^1$ is a functional group capable of reacting with the functions present on proteins, antibodies or on mineral or organic materials;
- X represents a single bond or a hydrocarbon-based chain consisting of at least one group chosen from alkylene groups and alkenylene groups optionally comprising at least one hetero atom, and from arylene groups;
- $R^2$ is a group $A^2$ that is anionic at neutral pH or an alkylene or alkenylene group containing from 1 to 4 carbon atoms and bearing at least one such group $A^2$, said alkylene or alkenylene group optionally comprising at least one hetero atom in the chain;
- $R^3$ represents H or an alkylene or alkenylene group containing from 1 to 5 carbon atoms and optionally containing at least one hetero atom in the chain, said group optionally bearing at least one group $A^3$ that is anionic at neutral pH;
- $R^4$ is a group corresponding to the formula $-(C)_n-C-Z^1-C-C-Z^2-C-A^4$ in which n is equal to 1 or 2, $Z^1$ and $Z^2$ represent, independently of each other, a hetero atom chosen from O and N, at least one being a nitrogen atom forming part of an aromatic heterocycle with the two carbon atoms surrounding it, and $A^4$ is a group that is anionic at neutral pH, in which the atom bearing the anionic charge is in the γ position relative to $Z^2$;
- $R^5$ is a group chosen from the groups defined for $R^4$ or from hydrocarbon-based chains $-C-C-E^1-C-C-E^2-C-A^5$ in which $E^1$ and $E^2$ represent, independently of each other, a hetero atom chosen from O and N, and $A^5$ is a group that is anionic at neutral pH, in which the atom bearing the anionic charge is in the γ position relative to $E^2$.

The hetero atom of the substituents X, $R^2$ and $R^3$ may especially be O or N.

The substituent $R^1$ may be chosen, for example, from amino, thio, cyano, isocyano, acridinyl, hydrazino, haloacetate, anhydride, triazo, carbonyl, nitrobenzoyl, sulfonyl, thionyl, halide, epoxide, aldehyde, imidazole, hydroxyphenyl, mercapto, N-succinimidyl ester, N-sulfosuccinimidyl ester, maleimido, hydroxyl, carboxyl, thiocyano, and isothiocyano groups. The amino, thio, carboxyl, maleimido, N-succinimidyl ester, N-sulfosuccinimidyl ester and isothiocyano groups are preferred.

When the group X is an alkylene or alkenylene group, it preferably contains from 1 to 10 carbon atoms. When X is an arylene group, it preferably contains from 5 to 10 carbon atoms. In the present text, the term "arylene group" means a group comprising one or more fused or unfused aromatic nuclei, the said nucleus (nuclei) optionally bearing one or more aliphatic hydrocarbon-based groups. Examples of arylene groups that may be mentioned include the groups —$C_6H_4$—, —$CH_2$—$C_6H_4$—$CH_2$—, —$C_6H_4$—$CH_2$—, —$C_6H_4$—$CH_2$—$C_6H_4$—, —$C_6H_3(CH_3)$—. X is advantageously chosen from a single bond or an alkylene or alkenylene group containing 2 or 3 carbon atoms.

The substituent $R^2$ is preferably a group $A^2$.

The substituent $R^3$ is preferably H or a $C_1$ to $C_3$ alkyl.

In the compounds of the present invention, each of the substituents $R^4$ and $R^5$ is a monovalent substituent. The substituents $R^4$ and $R^5$ do not together form a divalent group.

The substituent $R^4$ is a substituent that has light-absorbing properties and with which three chelate rings can be formed with a lanthanide. The substituents $R^4$ in which n is equal to 1 are preferred. As examples of substituents $R^4$ in which only one from among $Z^1$ and $Z^2$ is a nitrogen atom that forms part of an aromatic heterocycle, mention may be made of substituents in which one of the segments —C—$Z^i$—C— forms part of a heterocyclic group chosen from pyridyl, pyrimidinyl, quinolyl and isoquinolyl groups. The substituents $R^4$ in which $Z^1$ and $Z^2$ form part of an aromatic heterocyclic group are particularly advantageous. Examples of such substituents that may be mentioned include substituents in which each of the segments —C—$Z^1$—C— and —C—$Z^2$—C— forms part of a heterocyclic group chosen from pyridyl, pyrimidinyl, quinolyl and isoquinolyl groups, the two heterocyclic groups being linked by at least two carbon atoms separating $Z^1$ and $Z^2$. Examples of such segments —C—$Z^1$—C—C—$Z^2$—C— that may be mentioned include 2,2'-bipyridyl, 1,10-phenanthrolinyl, 2,2'-bisquinolyl, 2,2'-bisisoquinolyl and 2,2'-bipyrimidinyl groups, said groups possibly bearing alkyl or alkoxy substituents on at least one carbon atom of a heterocycle, preferably an alkyl or alkoxy group containing from 1 to 5 carbon atoms. By way of example, the formulae below represent, respectively, a 2,2'-bipyridyl group bearing a carboxyl, a monoalkylphosphonate, a monoarylphosphonate and a phosphonyl, or a phenanthrolinyl group bearing a carboxyl group.

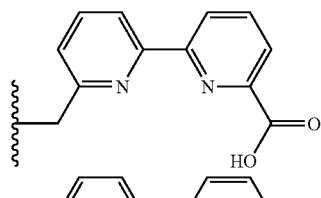

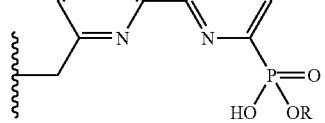

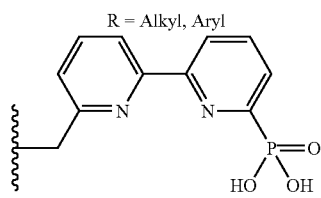

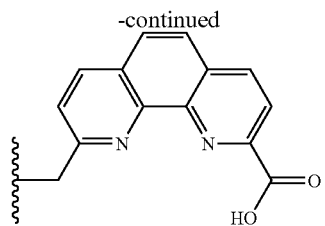

The substituent $R^5$ is a substituent with which three chelate rings can be formed with a lanthanide. Among the substituents $R^5$ consisting of a hydrocarbon-based chain —C—C—$E^1$—C—C—$E^2$—C—$A^5$, mention may be made of the following groups:

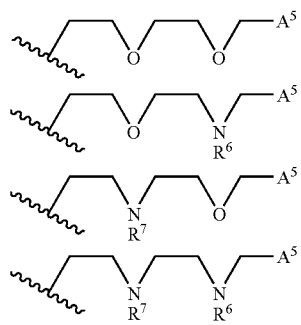

in which $R^6$ and $R^7$ represent alkyl chains preferably containing from 1 to 5 carbon atoms and optionally containing one or more hetero atoms. The compounds in which $R^4$ and $R^5$ are identical are particularly preferred.

As used herein, the expression "group that is anionic at neutral pH" means a functional group which, at neutral pH, is in anionic form, i.e. bears a negative charge. In a compound of the invention, the groups $A^2$, $A^3$, $A^4$ or $A^5$ that are anionic at neutral pH may be chosen, independently of each other, from —$CO_2H$, —$SO_3H$, —$P(O)(OR)OH$, —$P(O)R(OH)$ and —$P(O)(OH)_2$ groups in which R is an alkyl group (preferably of $C_1$ to $C_3$) or an aryl group (preferably of $C_5$ to $C_9$). Depending on the pH of the reaction medium, the compounds (I) are obtained in cationic, zwitterionic or anionic form. In acidic medium, the nitrogen bearing the substituents $R^4$ and $R^5$, and also optionally the hetero atoms $Z^1$, $Z^2$, $E^1$ and $E^2$, are in protonated form and the compound is in cationic form. In basic medium, the various groups $A^i$ are in the form of salts and the compound is in anionic form. At intermediate pH values, of about 6 to 8, the compound is in zwitterionic form.

A complex according to the present invention consists of a lanthanide ion Ln complexed with a ligand that corresponds to formula (I) above. The lanthanide ion is chosen from europium, terbium, samarium, dysprosium, erbium, ytterbium, neodymium and gadolinium ions. Europium, terbium, samarium or dysprosium will preferably be used if the complex is intended to be used for fluorescence marking, and europium, dysprosium or gadolinium will preferably be used when the complex is intended to be used as a contrast agent for NMRI.

In a complex according to the invention in which $R^4$ is —C—C—$Z^1$—C—C—$Z^2$—C—$A^4$, the 3 chelate rings form between the lanthanide cation and, respectively:

the N atom bearing $R^4$ and $R^5$, $Z^1$ and the carbon atoms that separate them;

$Z^1$, $Z^2$ and the two carbon atoms that separate them;

the end segment $Z^2$—C—$A^4$.

When $R^5$ is of the same type as $R^4$, it forms with the lanthanide ion chelates of the same type as those formed by $R_4$. When $R^5$ is of the type —C—C—$E^1$—C—C—$E^2$—C—$A^5$, three 5-membered chelate rings form between the lanthanide cation and, respectively:

the N atom bearing $R^4$ and $R^5$, $E^1$ and the two carbon atoms that separate them;

$E^1$, $E^2$ and the two carbon atoms that separate them;

the end segment $E^2$—C—$A^5$.

A compound (I) may be obtained via processes that are well known to those skilled in the art from commercial products or products described in the literature via the following scheme:

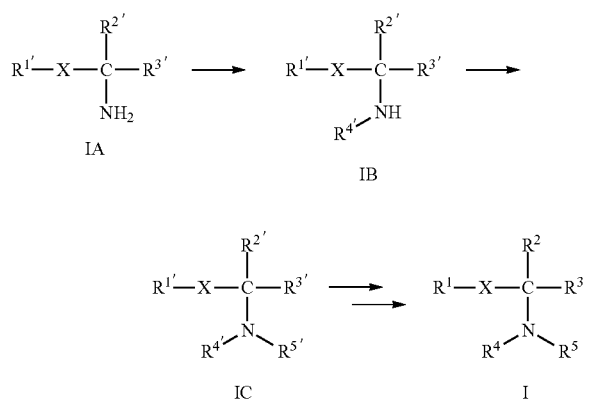

in which X, $R^1$, $R^2$, $R^3$, $R^4$ and $R^5$ have the meaning given above, and $R^{1\prime}$, $R^{2\prime}$, $R^{3\prime}$, $R^{4\prime}$ and $R^{5\prime}$ represent groups that are precursors of $R^1$, $R^2$, $R^3$, $R^4$ and $R^5$, respectively.

During the first two steps, the groups $R^{4\prime}$ and $R^{5\prime}$ are successively introduced onto a molecule IA containing X and the groups $R^{1\prime}$, $R^{2\prime}$ and $R^{3\prime}$ to obtain the compound IC.

During subsequent steps, the groups $R^{1\prime}$, $R^{2\prime}$, $R^{3\prime}$, $R^{4\prime}$ and $R^{5\prime}$ of the compound IC are converted, respectively, into groups $R^1$, $R^2$, $R^3$, $R^4$ and $R^5$.

When the groups $R^{4\prime}$ and $R^{5\prime}$ are identical in order to obtain identical groups $R^4$ and $R^5$, they are introduced simultaneously during the first step. When they are different, they are introduced in any order by reacting the molecule IA with two different reagents successively.

When compound (I) is a compound in which the groups $R^1$ and $R^2$ are carboxyl functions, the group $R^3$ is a hydrogen atom and the group X is a single bond, a methylene group or an ethylene group, the starting material IA that will advantageously be chosen is, respectively, diethyl aminomalonate, dimethyl aspartate and dimethyl glutamate, which are commercially available products.

When compound (I) is a compound in which:

the groups $R^1$ and $R^2$ are carboxyl functions, the group $R^3$ is a hydrogen atom, and the group X is a propylene or a para-substituted benzene, the starting material IA that may be used is, respectively, dimethyl 2-aminoadipate (the preparation of which is described by Lerch, E. et al, Helv. Chim. Acta, 1974, 57, 1584) and methyl (α-amino-4-methoxycarbonyl)benzene acetate (the preparation of which is described by Chauvel, E. et al, J. Med. Chem. 1994, 37, 1339).

When the groups $R^4$ and $R^5$ are identical and their segments —C—C—$Z^1$—C—C—$Z^2$—C— are derived from 2,2'-bipyridine, the starting material is reacted during the first step with 6-bromomethyl-6'-bromo-2,2'-bipyridine to obtain a dibromo compound IC. 6-bromomethyl-6'-bromo-2,2'-bipyridine may be obtained via a radical bromination reaction of 6-methyl-6'-bromo-2,2'-bipyridine with N-bromo-succinimide in benzene, 6-methyl-6'-bromo-2,2'-bipyridine being obtained according to the method described by Houghton M. et al, J. Chem. Soc., Dalton Trans. 1997, 2725. The reaction scheme for the first step of this particular case is given below.

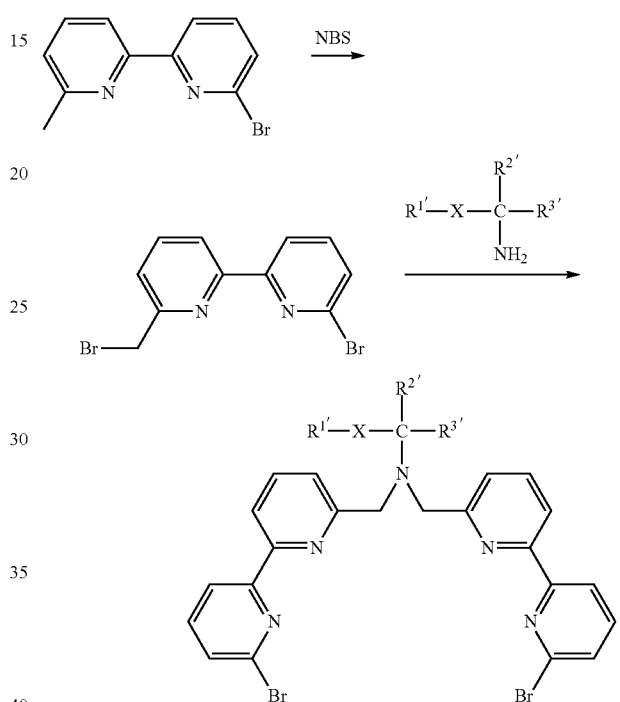

When the dibromo compound IC is subjected to a carboalkoxylation followed by a saponification with NaOH and an acidification with HCl, a compound (I) is obtained in which the groups $A^4$ and $A^5$ are carboxyl groups. The carboalkoxylation may be performed according to the process described by El-Ghayoury et al, J. Org. Chem., 2000, 65, 7757.

When the dibromo compound IC is reacted with a dialkyl phosphite (according to the method described by Penicaud et al, Tetrahedron Lett. 1998, 39, 3689), the dialkylphosphonate is obtained, each bromine atom being replaced with a group $P(O)(OR)_2$. The dialkylphosphonate gives, on saponification with NaOH in water, followed by acidification with HCl, a compound (I) in which the groups $A^4$ and $A^5$ are groups P(O)(OH)OR.

By reacting the dialkylphosphonate $P(O)(OR)_2$ with trimethylsilylbromide followed by a hydrolysis (according to the method described by McKenna C. et al., Tetrahedron Lett, 1977, 18, 155), a compound (I) is obtained in which the two anionic groups $A^4$ and $A^5$ are $P(O)(OH)_2$ groups. The same result may be obtained by means of an acid hydrolysis with HCl of the dialkylphosphonate $P(O)(OR)_2$.

The reaction scheme for the three operating modes above is given below.

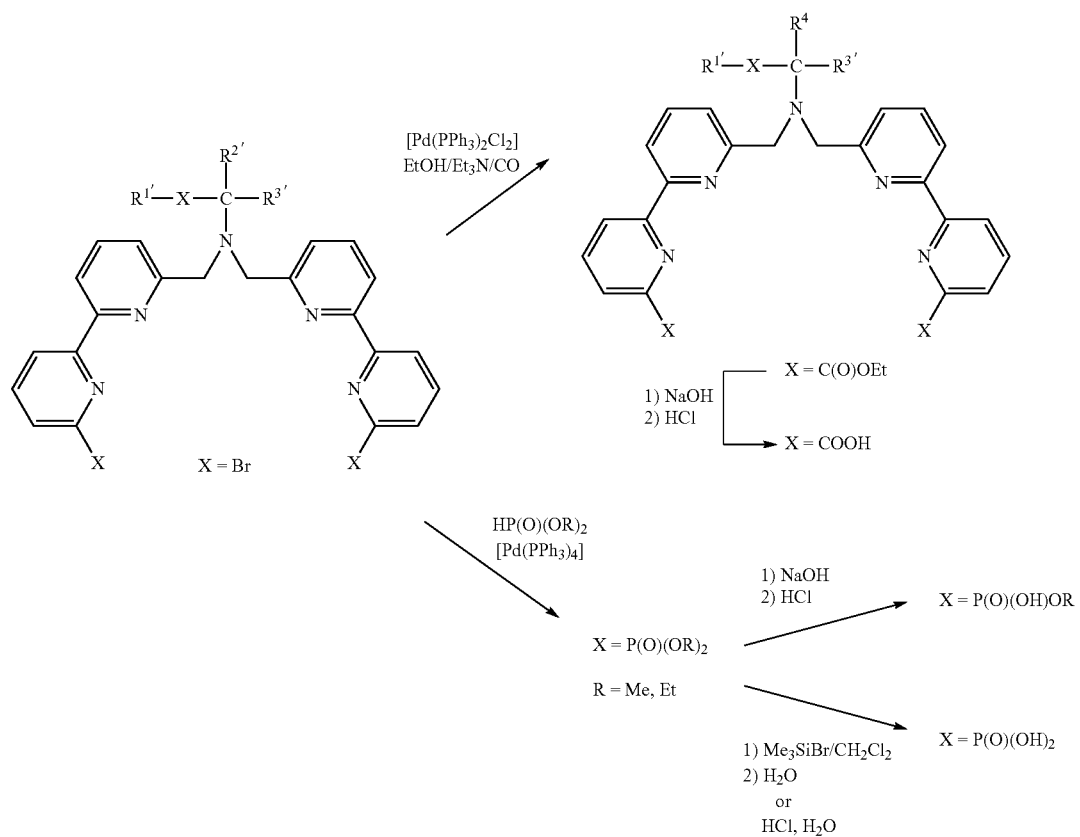

When the groups $R^4$ and $R^5$ are identical and their segments —C—C—$Z^1$—C—C—$Z^2$—C— are derived from 1,10-phenanthroline, the starting material is reacted during the first step with 2-bromomethyl-9-ethoxycarbonyl-1,10-phenanthroline. The preparation of 2-bromomethyl-9-ethoxycarbonyl-1,10-phenanthroline is described by Ulrich G. et al, (Tetrahedron Lett. 2001, 42, 6113). By subjecting the diester compound obtained to a saponification with NaOH, followed by an acidification with dilute HCl, a compound (I) is obtained in which the groups $A^4$ and $A^5$ are carboxyls. The reaction scheme is given below.

-continued

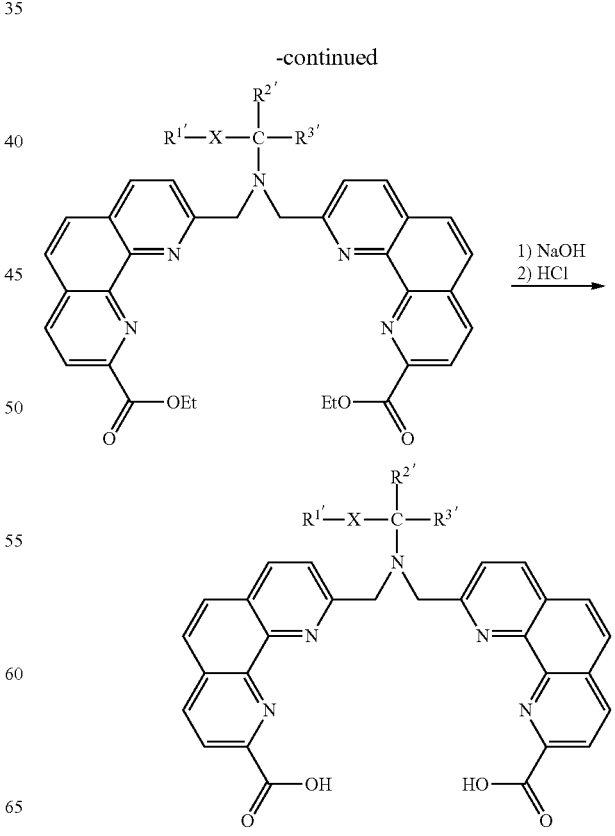

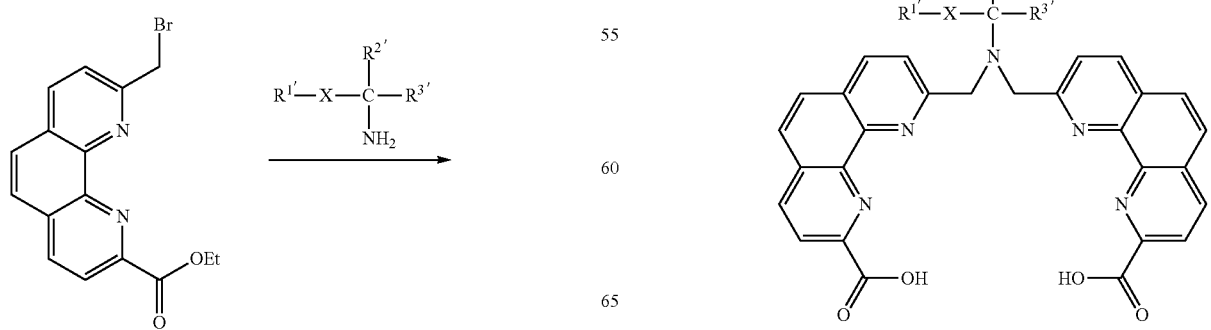

A desired substituent $R^1$ may be obtained by selecting either a starting compound that bears it or a starting compound that bears a precursor $R^{1'}$ of the desired substitutent. When a substituent $R^1$ is obtained from a precursor $R^{1'}$, the formation of the desired substituent may be performed on a compound of formula (IC) containing the precursor or on a complex formed with a lanthanide cation and a compound of formula (I) containing the precursor.

A substituent $R^1$ of the carboxyl type may be obtained via a saponification reaction starting with a precursor group $R^{1'}$ containing a carboxylic ester function. A substituent $R^1$ of the amino type may be obtained from the reduction of a precursor group $R^{1'}$ containing a nitro function. A substituent $R^1$ of the isothiocyano type may be obtained by reacting a precursor $R^{1'}$ containing an amino function with thiophosgene. A substituent $R^1$ of the maleimido type may be obtained by reacting a precursor $R^{1'}$ containing an amino function with the N-succinimidyl ester of 4-maleimidobutyric acid.

A substituent $R^1$ of the N-succinimidyl ester type may be obtained from a complex by activation of a carboxyl precursor with N-(3-dimethylaminopropyl)-N'-ethylcarbodiimide followed by a reaction with N-hydroxysuccinimide.

A complex according to the invention may be obtained by reacting a compound giving a lanthanide cation with a compound of formula (I). Examples of compounds giving a lanthanide cation that may be mentioned include lanthanide halide hydrates, lanthanide nitrate hydrates, lanthanide carbonates and lanthanide triflates. The reaction is performed in solution in a solvent. The solvent is preferably chosen from water, methanol, ethanol and acetonitrile.

In one preferred embodiment, compound (I) is reacted with the lanthanide ion precursor in a mixture of methanol and water at a pH ranging from 3 to 5, for a time of between 10 minutes and 24 hours, and at a temperature of between 25° C. and 80° C. Next, the pH of the solution is raised to 7.0 and the methanol is evaporated off before isolating the complex formed.

The complexes of the present invention may be used especially for fluorescence marking or for nuclear magnetic resonance imaging. For these applications, the preferred groups $R^1$ are amino, thio and carboxyl groups (which must be activated before the covalent coupling with the molecule to be marked), and maleimido, N-succinimidyl ester and isothiocyano groups (which can bind directly with the molecule to be marked).

The complexes of the present invention are useful for analyses or assays of compounds by marking of the compounds. The process consists in covalently bonding to the compound to be assayed a marker consisting of a complex according to the invention, and in detecting or quantifying the presence of the marked compound by means of the luminescence properties of the marker. Europium, terbium, samarium or dysprosium complexes are particularly preferred for this application.

When the lanthanide ion complexes according to the invention are intended to be used as relaxation agents for nuclear magnetic resonance, gadolinium, europium or dysprosium complexes are preferably used.

The present invention will be described in greater detail by means of the examples given below as illustrations, to which it is not, however, limited.

EXAMPLE 1

Preparation of Compound 1

Compound 1 was obtained according to the synthetic scheme below. The (S) isomer of the chosen glutamic ester may be replaced with the (R) isomer or a mixture of the two isomers.

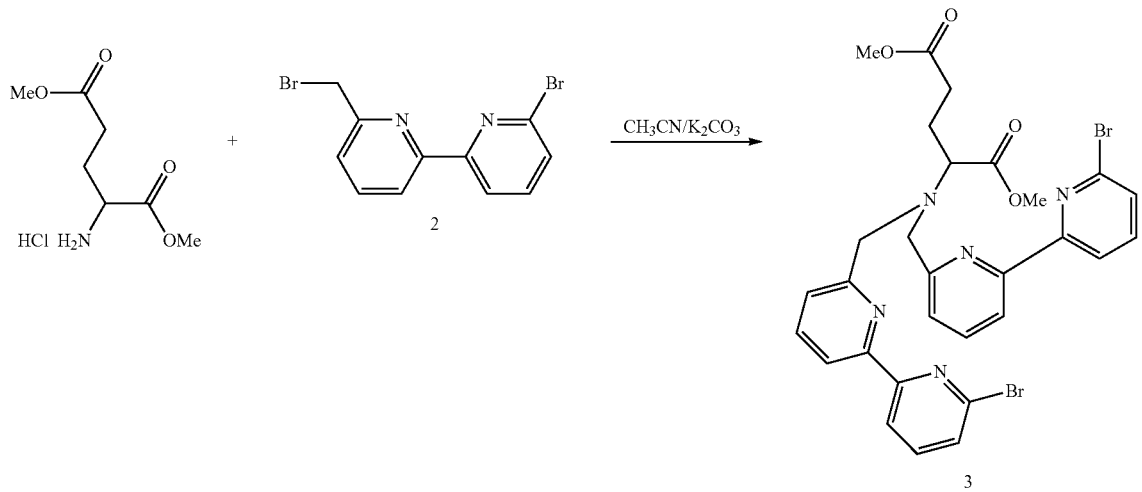

-continued

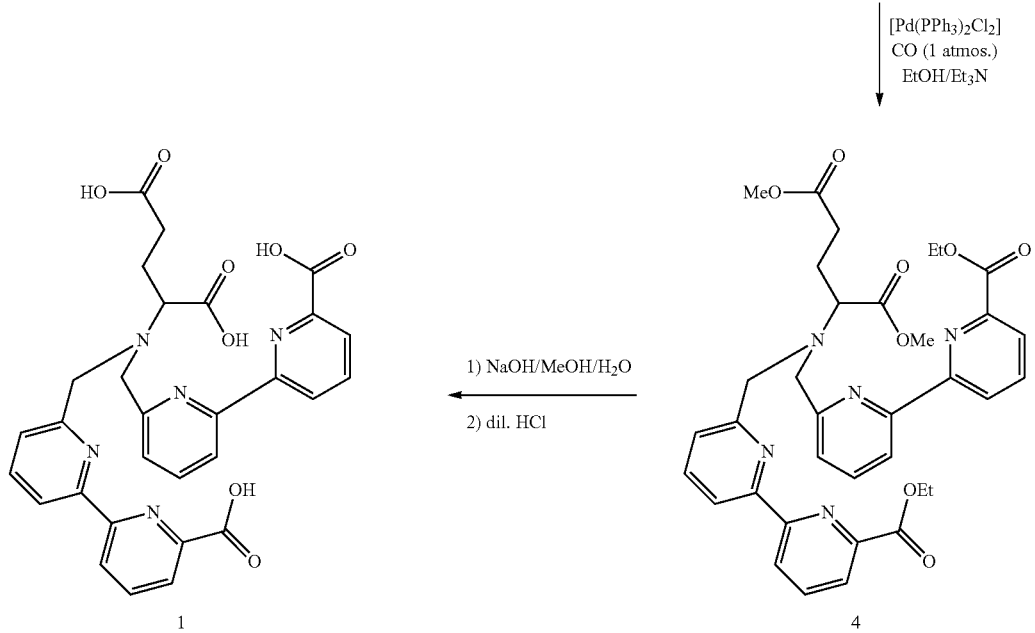

Preparation of Compound 2

Compound 2 was prepared according to the process described by S. Mameri, et al., in Synthesis, 2003, 17, 2713. 1.5 g (6.0 mmol) of 6-methyl-6'-bromo-2,2'-bipyridine, 66 mg (0.4 mmol) of azobisisobutyronitrile (AIBN) and 1.3 g (7.3 mmol) of N-bromosuccinimide are introduced into 90 mL of benzene in a 250 mL round-bottomed flask. The solution is refluxed for 2 hours 30 minutes by irradiating it with a standard 100 W halogen lamp. The solvent is evaporated off under reduced pressure and the solid residue is chromatographed on silica using a $CH_2Cl_2$/hexane gradient of from 50/50 to 100/0. 940 mg (2.9 mmol) of compound 2 are obtained (corresponding to a yield of 48%), which has the following characteristics:

$R_f$=0.42, $SiO_2$, $CH_2Cl_2$.

$^1$H-NMR ($CDCl_3$, 200 MHz): δ 4.61 (s, 2H), 7.48 (d, 1H, $^3J$=7.5 Hz), 7.50 (d, 1H, $^3J$=7.5 Hz), 7.68 (t, 2H, $^3J$=8.0 Hz), 7.83 (t, 1H, $^3J$=8.0 Hz), 8.33 (d, 1H, $^3J$=8.0 Hz), 8.44 (d, 1H, $^3J$=8.0 Hz).

$^{13}$C-NMR ($CDCl_3$, 50 MHz): δ 34.0, 120.1, 120.7, 124.0, 128.2, 138.1, 139.3, 141.6, 154.3, 156.4, 156.9.

Analyses calculated for $C_{11}H_8N_2Br_2$: C 40.28, H 2.46, N 8.54.

Found: C 40.12, H 2.34, N 8.44.

$FAB^+$/MS: 327 (50%), 329 (100%), 331(50%, $[2+H]^+$).

Preparation of Compound 3

470 mg (2.22 mmol) of dimethyl L-glutamate hydrochloride and 1.23 g of $K_2CO_3$ (8.90 mmol) are introduced into 100 mL of acetonitrile freshly distilled over $P_2O_5$, in a Schlenk tube under an argon atmosphere. The solution is heated at 80° C. for 30 minutes. 1.60 g (4.88 mmol) of compound 2 are added and the mixture is heated for 23 hours at 80° C. The solution is evaporated to dryness and the residue is redissolved with 100 mL of $CH_2Cl_2$ and 20 mL of water. The aqueous phase is washed with two portions of 20 mL of $CH_2Cl_2$ and the combined organic phases are dried over $MgSO_4$, filtered, and then evaporated to dryness. The solid residue is subjected to flash chromatography on silica (ϕ=5 cm, h=12 cm) with a mixture of $CH_2Cl_2$/MeOH (100/0 to 97/3) as eluent. 995 mg (1.49 mmol) of compound 3 are obtained (corresponding to a yield of 67%), which has the following characteristics:

$R_f$=0.34, $SiO_2$, $CH_2Cl_2$/MeOH (98/2).

$^1$H-NMR ($CDCl_3$, 200 MHz): δ 2.06-2.20 (m, 2H), 2.39-2.68 (m, 2H), 3.50 (s, 3H), 3.54-3.62 (m, 1H), 3.76 (s, 3H), 3.99-4.16 (m, 4H), 7.43-7.48 (m, 4H), 7.63 (t, 2H, $^3J$=8.0 Hz), 7.71 (t, 2H, $^3J$=8.0 Hz), 8.23 (d, 2H, $^3J$=8.0 Hz), 8.39 (d, 2H, $^3J$=8.0 Hz).

$^{13}$C-NMR ($CDCl_3$, 50 MHz): δ 24.8, 30.3, 51.5, 57.2, 62.1, 119.6, 119.7, 123.5, 127.8, 137.3, 139.1, 141.5, 153.8, 157.4, 159.1, 173.1, 173.4.

Analyses calculated for $C_{29}H_{27}N_5O_4Br_2$: C 52.04, H 4.07, N 10.46. Found: C 51.81, H 3.85, N 10.19.

$FAB^+$/MS: 670.2 ($[3+H]^+$, 100%).

Preparation of Compound 4

995 mg of (1.49 mmol) of compound 3 and 150 mg (0.21 mmol) of $[Pd(PPh_3)_2Cl_2]$ are introduced into 50 mL of ethanol and 50 mL of triethylamine in a 250 mL two-necked round-bottomed flask. The solution is heated at 70° C. for 15 hours by sparging with a flow of CO. The solution is evaporated to dryness, the solid obtained is redissolved in 100 mL of $CH_2Cl_2$ and filtered through Celite, and the organic phase is then extracted with 20 mL of water. The aqueous phase is washed with two portions of 20 mL of $CH_2Cl_2$ and the combined organic phases are dried over $MgSO_4$, filtered and then evaporated to dryness. The residue is subjected to flash chromatography on silica (ϕ=5 cm, h=10 cm) with a mixture of $CH_2Cl_2$/MeOH (99/1 to 90/10) as eluent. 588 mg (0.90 mmol) of 4 are obtained in the form of a slightly orange-colored oil (corresponding to a yield of 60%), which has the following characteristics:

$R_f$=0.30, $SiO_2$, $CH_2Cl_2$/MeOH (95/5).

$^1$H-NMR ($CDCl_3$, 200 MHz): δ 1.46 (t, 6H, $^3J$=7.0 Hz), 2.06-2.19 (m, 2H), 2.38-2.65 (m, 2H), 3.49 (s, 3H), 3.55-3.63 (m, 1H), 3.76 (s, 3H), 4.02-4.19 (m, 4H), 4.48 (q, 4H, $^3J$=7.0

Hz), 7.47 (d, 2H, $^3J$=8.0 Hz), 7.75 (t, 2H, $^3J$=8.0 Hz), 7.92 (t, 2H, $^3J$=8.0 Hz), 8.10 (d, 2H, $^3J$=8.0 Hz), 8.40 (d, 2H, $^3J$=8.0 Hz), 8.62 (d, 2H, $^3J$=8.0 Hz).

$^{13}$C-NMR (CDCl$_3$, 50 MHz): δ 14.3, 24.8, 30.4, 51.5, 57.2, 61.8, 62.0, 119.9, 123.5, 124.2, 124.8, 137.3, 137.7, 147.8, 154.6, 156.5, 159.0, 165.4, 173.2, 173.5.

Analyses calculated for $C_{35}H_{37}N_5O_8$: C 64.11, H 5.69, N 10.68.

Found: C 64.07, H 5.55, N 10.53.

FAB$^+$/MS: 656.2 ([4+H]$^+$, 100%).

Preparation of Compound 1

588 mg (0.90 mmol) of 4 and 144 mg (3.60 mmol) of NaOH are dissolved in a mixture of 50 mL of MeOH and 15 mL of water in a round-bottomed flask equipped with a condenser. The mixture is heated at 70° C. for 5 hours. The solution is evaporated to dryness and the solid is dissolved in 10 mL of water to which is slowly added 2N HCl solution to pH 2-3. The precipitate formed is isolated by centrifugation and dried under vacuum. 411 mg (0.60 mmol) of compound 1 are obtained in the form of a pale yellow hydrochloride 1.3HCl (corresponding to a yield of 67%), the characteristics of which are as follows:

$^1$H-NMR (CD$_3$OD, 300 MHz): δ 2.26-2.48 (m, 2H), 2.80-2.84 (m, 2H), 3.95-3.99 (m, 1H), 4.53-4.81 (m, 4H), 7.47 (d, 2H, $^3J$=7.5 Hz), 7.63 (t, 2H, $^3J$=8.0 Hz), 7.90 (t, 2H, $^3J$=8.0 Hz), 8.02 (d, 2H, $^3J$=7.5 Hz), 8.42 (d, 2H, $^3J$=7.5 Hz), 8.58 (d, 2H, $^3J$=7.5 Hz).

$^{13}$C-NMR (CD$_3$OD, 75 MHz): δ 23.1, 32.1, 57.0, 67.0, 122.3, 125.1, 125.9, 126.1, 139.7, 140.1, 149.0, 154.1, 155.5, 156.1, 168.0, 173.7, 176.4.

Analyses calculated for $C_{29}H_{25}N_5O_8$.3HCl: C 51.15, H 4.14, N 10.28. Found: C 51.01, H 4.43, N 9.95.

FAB$^+$/MS: 572.5 ([1+H]$^+$, 100%).

EXAMPLE 2

Preparation of Complex 5 of Formula [Eu.(1-4H).H$_2$O]Na

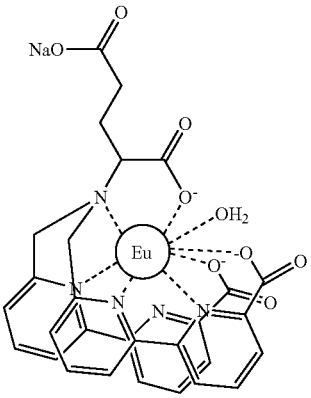

60 mg of 1.3HCl (88 μmol) are dissolved in a mixture of 30 mL of MeOH and 30 mL of water. To this solution is added a mixture of 36 mg (98 μmol) of EuCl$_3$.6H$_2$O dissolved in 3 mL of MeOH and 3 mL of water. The solution is heated at 70° C. for 1 hour. After cooling, the pH of the solution is raised to 7.4 with a 5% solution of NaOH in water. The solution is concentrated on a rotary evaporator until slight cloudiness appears. THF is then added until a substantial precipitate forms. The precipitate is isolated by centrifugation and then dried under vacuum to give 62 mg (74 μmol) of compound 5 (corresponding to a yield of 85%) in the form of a beige-colored solid, the characteristics of which are as follows:

$^1$H-NMR (D$_2$O/t-BuOH, 200 MHz, all the signals are in the form of broad singlets): δ −9.40 (1H), −8.95 (1H), −4.23 (2H), −3.17 (1H), −2.21 (1H), 1.88 (1H), 2.73 (1H), 4.17 (1H), 6.06 (1H), 7.12 (1H), 7.80 (1H), 7.88 (1H), 8.90 (1H), 9.60 (1H), 9.89 (1H), 11.08 (1H), 11.38 (1H), 12.01 (1H).

Analyses calculated for $C_{29}H_{21}NaN_5O_8Eu.5H_2O$: C 41.84, H 3.75, N 8.41. Found: C 41.93, H 3.62, N 8.44.

FAB$^+$/MS: 720.2 (80%), 722.2 (100%), [5-H$_2$O-Na+2H]$^+$.

IR (KBr, cm$^{-1}$): 3420, 1619, 1574, 1460, 1384, 1274.

Photophysical properties in water:

Absorption, $\lambda_{max}$ [nm] ($\epsilon_{max}$ [M$^{-1}$.cm$^{-1}$]): 320 (shoulder), 308 (19 700), 276 (8700), 267 (9700), 253 (14 400).

Emission: characteristic of europium compounds with fine bands at 581, 594, 615, 650 and 701 nm. Lifetime of the excited state: 0.62 ms. Quantum yield (reference [Ru(bipy)$_3$]$^{2+}$ in water): 8%. Lifetime of the excited state in deuterated water: 2.48 ms. Quantum yield in deuterated water: 35%.

EXAMPLE 3

Preparation of Complex 6 of Formula

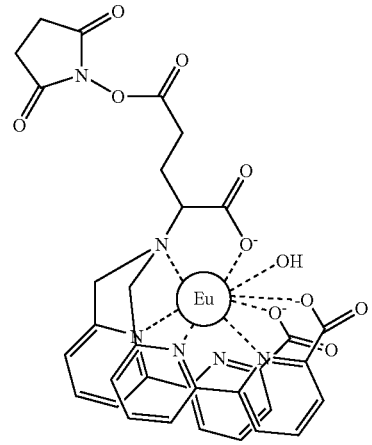

40 mg (48 μmol) of complex 5 and 12 mg (63 μmol) of ethyl-N,N-dimethyl-3-aminopropylcarbodiimide hydrochloride (EDCI.HCl) are suspended in 6 mL of DMSO. To this solution are added 7.0 mg (61 μmol) of N-hydroxysuccinimide. The solution is stirred at room temperature for 66 hours, during which the complex 5 dissolves, and a white precipitate then forms. The solid is isolated by centrifugation and dried under vacuum at 50° C. for 2 hours. 31 mg (34 μmol) of 6 are obtained (corresponding to a yield of 71%), the characteristics of which are as follows:

Analyses calculated for $C_{33}H_{25}EuN_6O_{10}.5H_2O$: C 43.67, H 3.89, N 9.26. Found: C 43.60, H 3.80, N 9.16.

FAB$^+$/MS: 720.1, 722.1 ([6-H$_2$O-C$_4$H$_4$NO$_2$+2H]$^+$, 100%), 817.1, 819.1 ([6-H$_2$O+H]$^+$, 30%).

IR (KBr disk, cm$^{-1}$): 3420, 1739, 1629, 1573, 1459, 1384.

Photophysical properties in water:

Absorption, $\lambda_{max}$ [nm] ($\epsilon_{max}$ [M$^{-1}$.cm$^{-1}$]): 320 (shoulder), 309 (20 000), 276 (10 000), 267 (10 500), 253 (16 000).

Emission: characteristic of europium compounds with fine bands at 581, 593, 615, 649 and 701 nm. Lifetime of the excited state: 0.63 ms. Quantum yield (reference [Ru(bipy)$_3$]

2+ in water): 8%. Lifetime of the excited state in deuterated water: 2.47 ms. Quantum yield in deuterated water: 34%.

EXAMPLE 4

Marking of an Amine with Complex 5

10 mg of complex 5 (13.1 μmol) are suspended in 5 mL of water. 3.5 mg (18.3 μmol) of EDCI.HCl and then 1.7 μL (13.2 μmol) of (+)-α-methylbenzylamine are added. After 15 minutes, and then after one hour, 1.7 μL of (+)-α-methylbenzylamine are added each time, at room temperature. Stirring is continued for 15 hours. The aqueous phase is washed with twice 10 mL of $CH_2Cl_2$ and then evaporated to dryness to give 14 mg of a pale yellow solid. After recrystallization from an MeOH/$Et_2O$ mixture, centrifugation and drying under vacuum, complex 7 (8.0 mg, 9.5 μmol) is recovered in the form of a cream-colored powder (73%).

ISI-TOF/MS: 847.0513 ([7-$H_2O$+Na]$^+$, 60%), 825.0912 ([7-$H_2O$+H]$^+$, 28%). The formula of complex 7 is shown below.

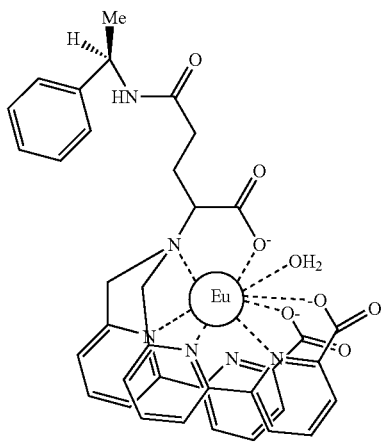

EXAMPLE 5

Marking of Bovine Serum Albumin BSA with Complex 6

Complex 6 (2.0 mg) is added to a solution of BSA (5.4 mg) in 1 mL of borate buffer (50 mM in water, pH=7.0) in order to obtain a 6/ASB mole ratio of 30:1. The solution is stirred at room temperature, leading to total dissolution of 6 after 2 hours. After stirring for 24 hours, the solution is deposited on a centrifuge filter (Centricon, Millipore, 30 KDa filter) and the volume of the solution is reduced to 200-300 μL by filtration. The solution is diluted with 3 mL of water and the volume is again reduced to 200-300 μL by filtration. This last operation is repeated 3 to 4 times, until the filtration waters are no longer luminescent under UV irradiation (absence of europium). The 200-300 μL of residual solution containing the marked protein and remaining on the filter are recovered and stored in a refrigerator at 4° C.

Characterization of the Marked BSA

The UV-Vis absorption spectrum of the aqueous solution of marked BSA shows a strong absorption due to the europium complexes, which partially overlaps the absorption due to the protein ($\lambda_{max}$=278 nm, $\epsilon_{max}$=38 000 $M^{-1}.cm^{-1}$). On excitation of the solution in the absorption band of the bipyridines (308 nm), a typical emission spectrum of europium compounds is observed, with a mean lifetime of the excited state of 1.1 ms (the decrease is not purely mono-exponential) and a luminescence quantum yield of 13% is observed.

Characterization by mass spectrometry in MALDI-TOF mode (Matrice Assisted Laser Desorption Ionization-Time Of Fly) is performed in the following manner. An aqueous solution of marked BSA is treated with 1% trifluoroacetic acid to decomplex the europium, and the protein is then adsorbed onto a chromatography column whose hydrophobic solid phase consists of $C_4$ chain. After washing with water, the protein is released with acetonitrile and then analyzed by MALDI-TOF (α-cyano-4-hydroxycinnamic acid matrix). The mean mass obtained for the europium-free marked protein is 71 700 Da (BSA, M=66 610 Da), leading to a markers/BSA mole ratio of 9/1 in the marked protein.

EXAMPLE 6

Preparation of Complex 8 of Formula [Tb.(1-4H).$H_2O$]Na

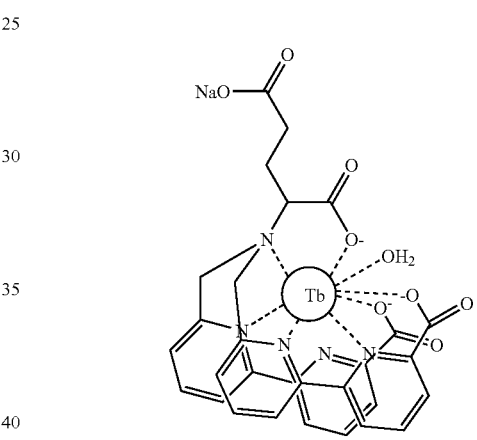

40 mg (59 μmol) of compound 1.3HCl are dissolved in a mixture of 30 mL of MeOH and 30 mL of water in a 250 mL round-bottomed flask equipped with a condenser. To this solution are added 25 mg (67 μmol) of $TbCl_3.6H_2O$ dissolved in 5 mL of MeOH and 5 mL of water. The solution is heated at 70° C. for one hour. After cooling, the pH of the solution is raised to 7.2 with a 1% solution of NaOH in water. The solution is concentrated on a rotary evaporator until slight cloudiness appears, and THF is then added until a substantial precipitate forms. A pale yellow solid is isolated by centrifugation and then dried under vacuum. 46 mg (56 μmol) of complex 8 are obtained (corresponding to a yield of 95%), the characteristics of which are as follows:

Analyses calculated for $C_{29}H_{21}NaN_5O_8Tb.4H_2O$: C 42.40, H 3.56, N 8.53. Found: C 42.28, H 3.31, N 8.38.

$FAB^-$/MS: 668.2 ([8-$H_2O$-$CH_2COONa$]$^-$, 100%), 726.2 ([8-$H_2O$-Na]$^-$, 30%).

IR (KBr disk, $cm^{-1}$): 3428, 1592, 1574, 1466, 1416, 1387.

Photophysical properties in water:

Absorption, $\lambda_{max}$ [nm] ($\epsilon_{max}$ [$M^{-1}.cm^{-1}$]): 320 (shoulder), 308 (20 800), 277 (8900), 267 (10 400), 253 (15 000).

Emission: characteristic of terbium compounds with fine bands at 487, 543, 583 and 621 nm. Lifetime of the excited state: 1.48 ms. Quantum yield (reference: quinine sulfate in 1N $H_2SO_4$): 31%. Lifetime of the excited state in deuterated water: 2.53 ms. Quantum yield in deuterated water: 53%.

EXAMPLE 7

Preparation of Complex 9 of Formula

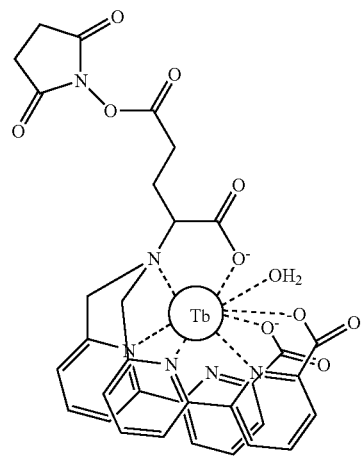

50 mg (61 µmol) of complex 8 are suspended in 5 mL of DMSO in a 10 mL round-bottomed flask. To this solution are added 9 mg (78 µmol) of N-hydroxysuccinimide and 13 mg (68 µmol) of ethyl-N,N-dimethyl-3-aminopropylcarbodiimide hydrochloride (EDCI.HCl). The solution is stirred at room temperature for 138 hours, during which time complex 8 dissolves and a white precipitate then forms. The solid is isolated by centrifugation, washed with THF and dried under vacuum. Addition of THF to the mother liquors causes the formation of a further precipitate, which is recovered by centrifugation. 49 mg (55 µmol) of complex 9 are obtained in total (corresponding to a yield of 90%), the characteristics of which are as follows:

Analyses calculated for $C_{33}H_{25}N_6O_{10}Tb.4H_2O$: C 44.21, H 3.71, N 9.29. Found: C 44.01, H 3.42, N 9.29.

$FAB^+/MS$: 726.2 ($[9-H_2O-C_4H_4NO_2]^+$, 15%), 825.5 ($[9-H_2O+H]^+$, 100%).

IR (KBr disk, $cm^{-1}$): 3433, 1741, 1624, 1594, 1574, 1464, 1419, 1375.

Photophysical Properties in Water

Absorption, $\lambda_{max}$ [nm] ($\epsilon_{max}$ [$M^-.cm^{-1}$]): 308 (18 700), 276, 267, 253.

Emission: characteristic of terbium compounds with fine bands at 487, 543, 583 and 621 nm. Lifetime of the exited state: 1.50 ms. Quantum yield (reference: quinine sulfate in 1N $H_2SO_4$): 34%. Lifetime of the excited state in deuterated water: 2.42 ms. Quantum yield in deuterated water: 62%.

EXAMPLE 8

Marking of Bovine Serum Albumin BSA with Complex 9 and Revelation by Time-resolved Luminescence Microscopy The marking of the bovine serum albumin was performed according to the method described in Example 5, replacing the complex 6 with complex 9.

Determination of the Markers/BSA Mole Ratio

The markers/BSA mole ratio (number of complexes 9 covalently bonded to BSA) is determined by differential absorption at 308 nm. The molar absorption coefficients of native BSA and of the marked BSA are measured at 308 nm. The difference between these two values is divided by the molar absorption coefficient of 9 at 308 nm, to give a markers/BSA mole ratio of 6/1 in the marked protein.

FIG. 1 shows droplets about 750 microns in diameter containing BSA marked with compound 9 (left-hand and right-hand columns on each image) and a fluorescein-marked antibody (middle column on each image) serving as reference (fluorescein-marked rabbit immunoglobulin produced by Dako-Immunoglobuline under the product code F-123). The image obtained by conventional fluorescence microscopy (left) reveals the fluorescence of the two compounds. The image obtained by time-resolved luminescence microscopy (delay=0.5 ms, integration time=5.0 ms) shows the disappearance of the fluorescence of the reference compound, whereas the luminescence of the marked BSA persists.

EXAMPLE 9

Preparation of Complex 10 of Formula
[Gd.(1-4H).$H_2$O]Na

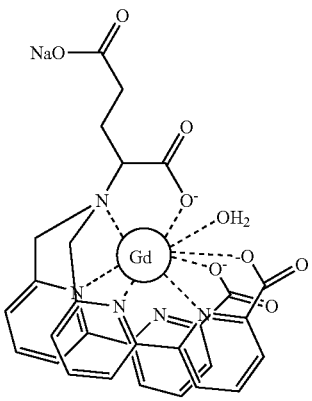

30 mg (44 µmol) of compound 1.3HCl are dissolved in a mixture of 25 mL of MeOH and 25 mL of water in a 100 mL round-bottomed flask equipped with a condenser. To this solution are added 19 mg (51 µmol) of $GdCl_3.6H_2O$ dissolved in 5 mL of MeOH and 5 mL of water. The solution is heated at 70° C. for one hour. After cooling, the pH of the solution is raised to 7.5 with a 0.5% solution of NaOH in water. The solution is concentrated on a rotary evaporator until slight cloudiness appears, and THF is then added until a substantial precipitate forms. The pale yellow solid is isolated by centrifugation and then dried under vacuum to give 30 mg (37 µmol) of complex 10 (corresponding to a yield of 85%), the characteristics of which are as follows:

Analyses calculated for $C_{29}H_{21}GdNaN_5O_8.3H_2O$: C 43.44, H 3.39, N 8.73. Found: C 43.35, H 3.17, N 8.55.

$FAB^-/MS$: 667.2 ($[10-H_2O-CH_2COONa]^-$, 100%), 725.2 ($[10-H_2O-Na]^-$, 45%).

IR (KBr disk, $cm^{-1}$): 3422, 1637, 1592, 1459, 1419, 1385.

EXAMPLE 10

Preparation of Complex 11 of Formula

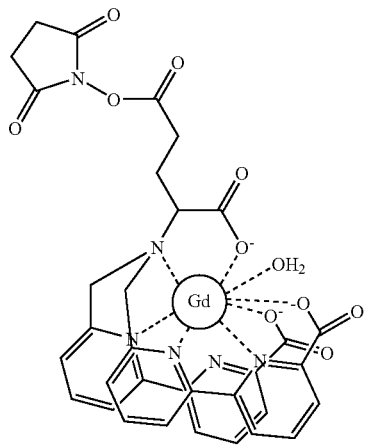

50 mg (62 µmol) of compound 10 are suspended in 5 mL of DMSO in a 10 mL round-bottomed flask. To this solution are added 9 mg (78 µmol) of N-hydroxysuccinimide and 15 mg (78 µmol) of ethyl-N,N-dimethyl-3-aminopropylcarbodiimide hydrochloride (EDCI.HCl). The solution is stirred at room temperature for 48 hours, during which time complex 10 dissolves and a white precipitate then forms. The solid is isolated by centrifugation, washed with THF and dried under vacuum. The addition of THF to the mother liquors causes the formation of additional precipitate, which is recovered by centrifugation. 45 mg (51 µmol) of complex 11 are obtained in total (corresponding to a yield of 82%), the characteristics of which are as follows:

Analyses calculated for $C_{33}H_{25}GdN_6O_{10} \cdot 3H_2O$: C 45.20, H 3.56, N 9.37. Found: C 45.02, H 3.18, N 9.21.

FAB$^+$/MS: 726.5 ([11-H$_2$O-C$_4$H$_4$NO$_2$+2H]$^+$, 20%), 824.2 ([11-H$_2$O+H]$^+$, 100%).

IR (KBr disk, cm$^{-1}$): 3435, 1741, 1623, 1573, 1465, 1420, 1376.

EXAMPLE 11

Preparation of Compound 12

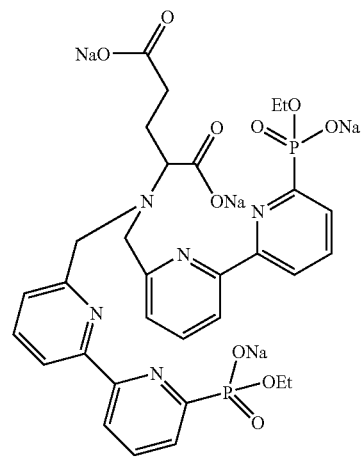

This compound is obtained in two steps from compound 3 according to the following synthetic scheme:

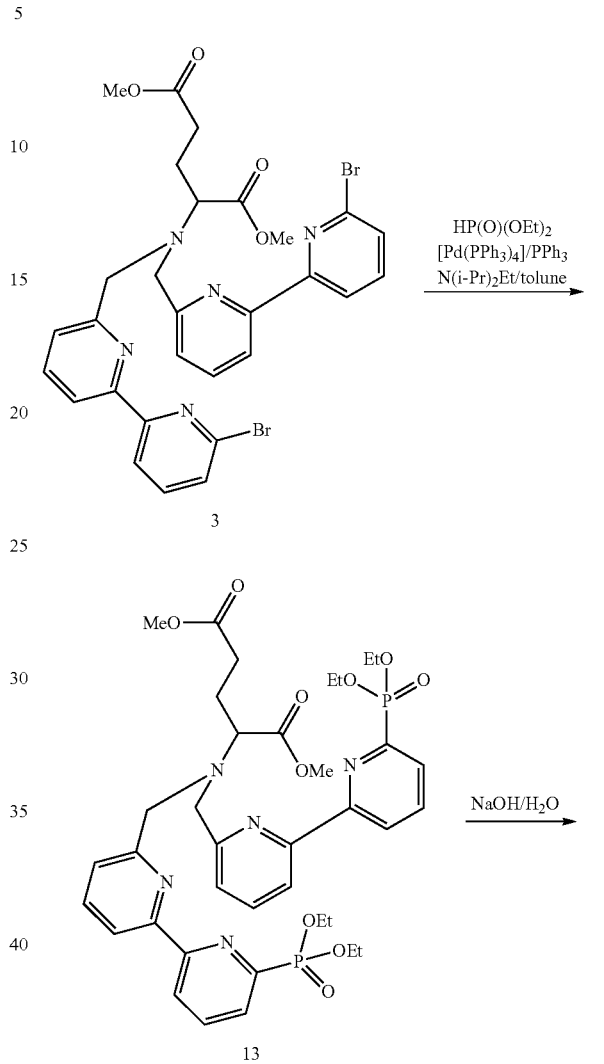

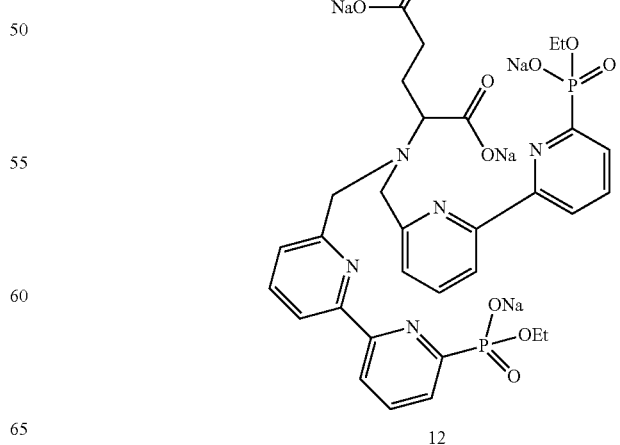

21
Preparation of Compound 13

200 mg (0.30 mmol) of compound 3, 90 μL (0.70 mmol) of diethyl phosphite, 78 mg (0.30 mmol) of PPh$_3$ and 300 μL of freshly distilled diisopropylethylamine are introduced into 10 mL of toluene in a Schlenk tube under an argon atmosphere. The solution is degassed with argon for 20 minutes. 34 mg (0.03 mmol) of Pd(PPh$_3$)$_4$ are added and the solution is heated at 100° C. for 16 hours. 40 μL (0.31 mmol) of diethyl phosphite and 34 mg (0.03 mmol) of Pd(PPh$_3$)$_4$ are added and the solution is again heated at 100° C. for 16 hours. The solution is evaporated to dryness. The solid residue is purified by flash chromatography on silica (φ=3 cm, h=15 cm) with a CH$_2$Cl$_2$/MeOH mixture (99/1 to 95/5) as eluent. The pure fractions are evaporated, dissolved in 30 mL of CH$_2$Cl$_2$ and washed with 10 mL of water. The organic phase is dried over MgSO$_4$, filtered and evaporated. 72 mg (0.09 mmol) of compound 13 are obtained (corresponding to a yield of 31%) in the form of an oil having the following characteristics:

R$_f$=0.56, SiO$_2$, CH$_2$Cl$_2$/MeOH (90/10).

$^1$H-NMR (CDCl$_3$, 200 MHz): δ 1.35 (t, 12H, $^3$J=7.0 Hz), 2.02-2.22 (m, 2H), 2.37-2.71 (m, 2H), 3.47 (s, 3H), 3.54-3.61 (m, 1H), 3.75 (s, 3H), 4.01-4.17 (m, 4H), 4.18-4.36 (m, 8H), 7.47 (d, 2H, $^3$J=7.5 Hz), 7.73 (t, 2H, $^3$J=8.0 Hz), 7.81-7.97 (m, 4H), 8.32 (d, 2H, $^3$J=7.5 Hz), 8.59 (dt, 2H, $^3$J$_{H-H}$=7.0 Hz, $^3$J$_{H-P}$=$^4$J$_{H-H}$=2.0 Hz).

$^{13}$C-NMR (CDCl$_3$, 50 MHz): δ 16.3, 16.4, 24.7, 30.3, 51.4, 57.1, 61.9, 63.0, 63.1, 119.6, 123.2 (2), 123.4, 127.4, 127.9, 136.7, 137.0, 137.2, 149.0, 153.5, 154.5, 156.5, 156.9, 159.0, 173.1, 173.4.

$^{31}$P-NMR (CDCl$_3$, 162 MHz): δ 11.73.

Preparation of Compound 12

51 mg (65 μmol) of compound 13 are dissolved in 6 mL of a 0.05 N solution of NaOH in water, in a 50 mL round-bottomed flask equipped with a condenser. The mixture is heated at 100° C. for 19 hours. After cooling, the aqueous phase is extracted with 4 portions of 5 mL of CH$_2$Cl$_2$ and then evaporated to dryness. The product precipitates from an H$_2$O/THF mixture. 45 mg (51 μmol) of compound 12 are obtained (corresponding to a yield of 79%) in the form of a cream-colored powder, the characteristics of which are as follows:

$^1$H-NMR (D$_2$O/$^t$BuOH, 300 MHz): δ 1.18 (t, 6H, $^3$J=7.0 Hz), 2.06-2.27 (m, 2H), 2.37-2.58 (m, 2H), 3.50 (t, 3H, $^3$J=7.5 Hz), 3.86-3.99 (m, 4H), 4.02-4.24 (m, 4H), 7.48 (d, 2H, $^3$J=7.0 Hz), 7.59-7.81 (m, 10H).

$^{13}$C-NMR (D$_2$O/$^t$BuOH, 75 MHz): δ 16.4, 16.5, 27.8, 35.6, 59.8, 62.4, 62.5, 71.6, 121.2, 124.0, 124.1, 125.7, 127.1, 127.4, 138.0, 138.2, 138.5, 154.6, 155.0, 156.3, 156.6, 157.8, 160.6, 181.1, 183.6.

$^{31}$P-NMR (D$_2$O, 162 MHz): δ 10.17.

Analyses calculated for C$_{31}$H$_{31}$N$_5$Na$_4$O$_{10}$P$_2$·5H$_2$O: C 42.43, H 4.71, N 7.98. Found: C 42.35, H 4.55, N 7.78.

FAB$^+$/MS: 764.2 ([12-Na]$^+$, 10%).

22
EXAMPLE 12

Preparation of Complex 14 of Formula

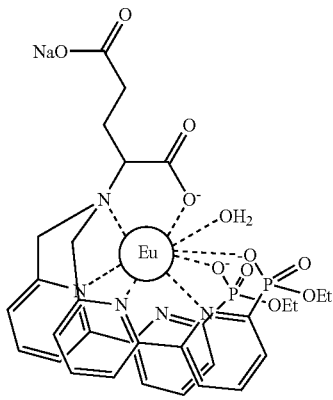

19 mg (22 μmol) of compound 12 are dissolved in 35 mL of water in a 50 mL round-bottomed flask equipped with a condenser. The pH is adjusted to 3.1 with dilute HCl solution. To this solution are added 9 mg (25 μmol) of EuCl$_3$·6H$_2$O dissolved in 5 mL of water. The solution is heated at 80° C. for one hour. After cooling, the solution is filtered through Celite and the pH is raised to 7.1 with a 0.5% solution of NaOH in water. The solution is evaporated to dryness and the product precipitates from an H$_2$O/THF mixture. The pale yellow solid is isolated by centrifugation and then dried under vacuum, to give 9 mg (10 μmol) of complex 14 (corresponding to a yield of 47%), the characteristics of which are as follows:

FAB$^+$/MS: 848.2 ([14-H$_2$O-Na]$^+$, 35%).

EXAMPLE 13

Preparation of Compound 15

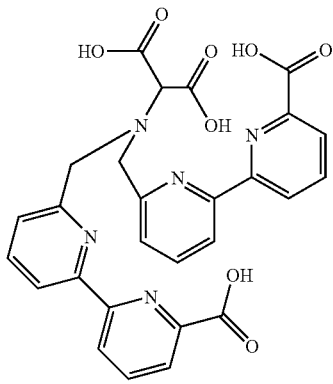

This compound is obtained in three steps according to the following synthetic scheme:

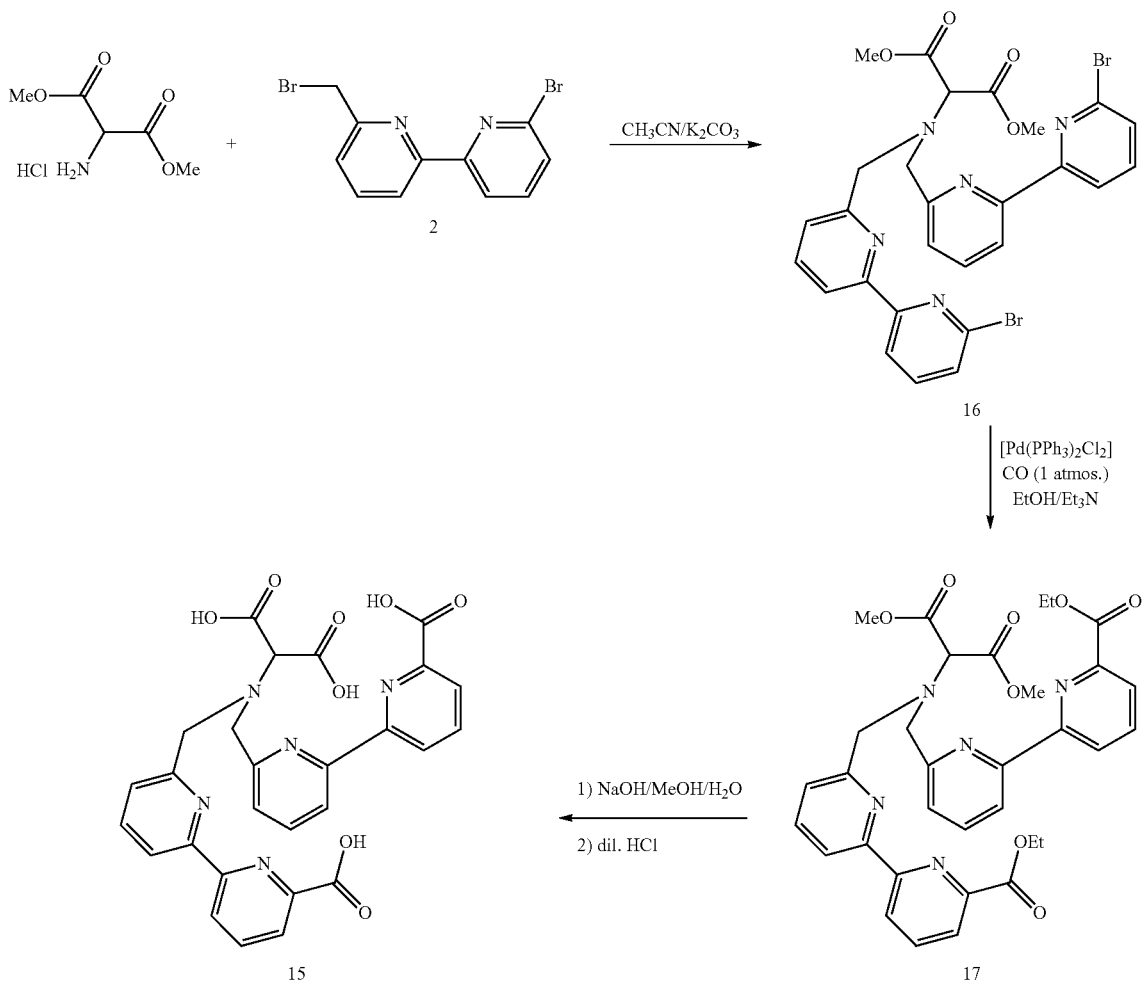

Preparation of Compound 16

450 mg (2.13 mmol) of diethyl aminomalonate hydrochloride and 1.18 g (8.54 mmol) of $K_2CO_3$ are introduced into 150 mL of freshly distilled acetonitrile in a 500 mL round-bottomed Schlenk flask under an argon atmosphere. The solution is heated at 80° C. for one hour. 1.46 g (4.45 mmol) of compound 2 are added and the mixture is heated for 21 hours at 80° C. The solution is evaporated to dryness and the residue is redissolved with 100 mL of $CH_2Cl_2$ and 20 mL of water. The aqueous phase is washed with two portions of 20 mL of $CH_2Cl_2$ and the combined organic phases are dried over $MgSO_4$, filtered and then evaporated to dryness. The solid residue is purified by flash chromatography on silica (φ=4 cm, h=14 cm) with a $CH_2Cl_2$/MeOH mixture (100/0 to 99/1) as eluent. 794 mg (1.19 mmol) of compound 16 are obtained (corresponding to a yield 56%) in the form of a pale yellow powder having the following characteristics:

$R_f$=0.57, $SiO_2$, $CH_2Cl_2$/MeOH (97/3).

$^1$H-NMR (CDCl$_3$, 200 MHz): δ 1.26 (t, 6H, $^3$J=7.0 Hz), 4.22 (s, 4H), 4.23 (q, 4H, $^3$J=7.0 Hz), 4.47 (s, 1H), 7.43 (dd, 2H, $^3$J=7.5 Hz, $^4$J=0.5 Hz), 7.60 (t, 2H, $^3$J=7.5 Hz), 7.62 (d, 2H, $^3$J=7.5 Hz), 7.75 (t, 2H, $^3$J=8.0 Hz), 8.22 (dd, 2H, $^3$J=7.5 Hz, $^4$J=1.0 Hz), 8.37 (dd, 2H, $^3$J=7.5 Hz, $^4$J=1.0 Hz).

$^{13}$C-NMR (CDCl$_3$, 50 MHz): δ 14.1, 58.0, 61.4, 67.1, 119.7, 123.4, 127.7, 137.4, 139.0, 141.4, 153.5, 157.4, 158.9, 168.1.

Analyses calculated for $C_{29}H_{27}Br_2N_5O_4$: C 52.04, H 4.07, N 10.46. Found: C 51.93, H 3.93, N 10.31.

FAB$^+$/MS: 670.2 (100%), 672.2 (50%), [16+H]$^+$.

Preparation of Compound 17

778 mg (1.16 mmol) of compound 16 and 82 mg (0.12 mmol) of [Pd(PPh$_3$)$_2$Cl$_2$] are introduced into 75 mL of ethanol and 75 mL of triethylamine in a 250 mL two-necked round-bottomed flask. The solution is heated at 70° C. for 16 hours while sparging with a stream of CO. The solution is evaporated to dryness, the solid obtained is redissolved in 75 mL of $CH_2Cl_2$ and filtered through Celite, and the organic phase is then washed with 15 mL of water. The aqueous phase is extracted with two portions of 20 mL of $CH_2Cl_2$ and the combined organic phases are dried over $MgSO_4$, filtered and then evaporated to dryness. The residue is purified by flash chromatography on silica ((φ=3 cm, h=16 cm) with a $CH_2Cl_2$/MeOH mixture (99.5/0.5 to 90/10) as eluent. The fractions containing compound 17 with triphenylphosphine oxide are dissolved in 40 mL of $CH_2Cl_2$ and extracted with four portions of HCl 3N. The combined aqueous phases are neutralized with NaOH and then extracted with three portions of 30 mL of $CH_2Cl_2$. The combined organic phases are dried over $MgSO_4$, filtered and then evaporated to dryness. 522 mg (0.80 mmol) of compound 17 are obtained in the form of a colorless oil (corresponding to a yield of 68%), which has the following characteristics:

$R_f$=0.55, $SiO_2$, $CH_2Cl_2$/MeOH (90/10).

$^1$H-NMR (CDCl$_3$, 200 MHz): δ 1.26 (t, 6H, $^3$J=7.0 Hz), 1.45 (t, 6H, $^3$J=7.0 Hz), 4.23 (q, 4H, $^3$J=7.0 Hz), 4.24 (s, 4H), 4.47 (q, 4H, $^3$J=7.0 Hz), 4.48 (s, 1H), 7.64 (dd, 2H, $^3$J=7.5 Hz, $^4J=0.5$ Hz), 7.80 (t, 2H, $^3J=8.0$ Hz), 7.91 (t, 2H, $^3J=7.5$ Hz), 8.09 (dd, 2H, $^3J=7.5$ Hz, $^4J=1.0$ Hz), 8.40 (dd, 2H, $^3J=7.5$ Hz, $^4J=0.5$ Hz), 8.62 (dd, 2H, $^3J=8.0$ Hz, $^4J=1.5$ Hz).

$^{13}$C-NMR (CDCl$_3$, 50 MHz): δ 14.1, 14.3, 58.0, 61.4, 61.8, 67.1, 120.0, 123.4, 124.2, 124.7, 137.5, 137.7, 147.7, 154.4, 156.5, 158.8, 165.3, 168.2.

Analyses calculated for $C_{35}H_{37}N_5O_8$: C 64.11, H 5.69, N 10.68.

Found: C 63.81, H 5.43, N 10.43.

FAB$^+$/MS: 496.2 (35%), 656.1 ([17+H]$^+$, 100%).

Preparation of Compound 15

103 mg (0.16 mmol) of compound 17 and 50 mg (1.25 mmol) of NaOH are dissolved in a mixture of 10 mL of MeOH and 5 mL of water in a 50 mL round-bottomed flask equipped with a condenser. The mixture is heated at 70° C. for 5 hours. The solution is evaporated to dryness and the solid is dissolved in 8 mL of water, to which is slowly added, at 0° C., 1N HCl solution until an abundant precipitate of the product is obtained (pH=4-5). The precipitate is isolated by centrifugation and dried under vacuum. 59 mg (0.08 mmol) of 15.3HCl hydrochloride hydrate are obtained (corresponding to a yield of 53%) in the form of a white powder, the characteristics of which are as follows:

$^1$H-NMR (NaOD/$^t$BuOH, 300 MHz): δ 3.75 (s, 4H), 4.04 (s, 1H), 6.84 (d, 2H, $^3J=7.5$ Hz), 7.15-7.26 (m, 4H), 7.32 (d, 2H, $^3J=7.5$ Hz), 7.42 (t, 2H, $^3J=7.5$ Hz), 7.56 (d, 2H, $^3J=7.5$ Hz).

$^{13}$C-NMR (NaOD/$^t$BuOH, 75 MHz): δ 60.3, 79.4, 119.9, 122.9, 124.1, 124.4, 138.2, 138.6, 152.8, 153.7, 154.0, 158.7, 168.6, 172.3, 177.3.

Analyses calculated for $C_{27}H_{21}N_5O_8$.3HCl.3H$_2$O: C 45.87, H 4.28, N 9.91. Found: C 45.75, H 4.09, N 9.78.

FAB$^+$/MS: 544.2 ([15+H]$^+$, 20%).

EXAMPLE 14

Preparation of Complex 18 of Formula

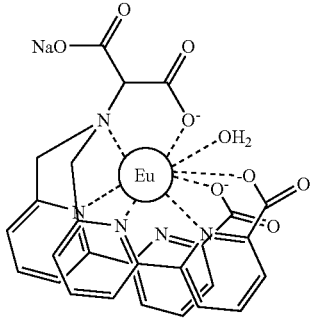

15 mg of 15.3HCl.3H$_2$O (21 µmol) are dispersed in a mixture of 10 mL of MeOH and 10 mL of water in a 10 mL round-bottomed flask. To this solution are added 10 mg (27 µmol) of EuCl$_3$.6H$_2$O dissolved in 5 mL of MeOH and 5 mL of water. The solution is heated at 70° C. for one hour. After cooling, the pH of the solution is raised to 7.3 with a 0.5% solution of NaOH in water. The solution is concentrated on a rotary evaporator until a precipitate forms. The white solid is isolated by centrifugation and then dried under vacuum to give 14 mg (19 µmol) of compound 18 (corresponding to a yield of 90%), the characteristics of which are as follows:

FAB$^-$/MS: 692.3 ([18-H$_2$O-Na]$^-$, 100%).

IR (KBr disk, cm$^{-1}$): 3442, 1626, 1588, 1460, 1411, 1373.

EXAMPLE 15

Preparation of Complex 19 of Formula

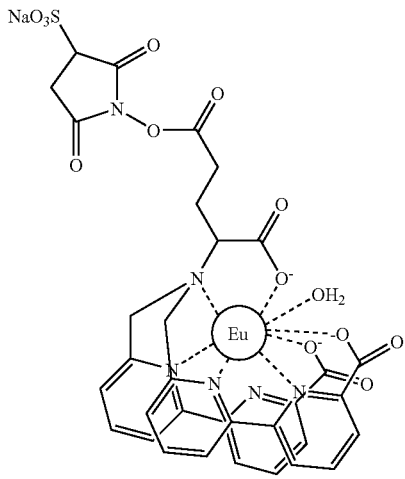

18 mg (22 µmol) of complex 5 are suspended in 5 mL of DMSO in a 10 mL round-bottomed flask. To this solution are added 6 mg (26 µmol) of the monosodium salt of N-hydroxysuccinimide-3-sulfonic acid hydrate and 5 mg (26 µmol) of ethyl-N,N-dimethyl-3-aminopropylcarbodiimide hydrochloride (EDCI.HCl). The solution is stirred at room temperature for 46 hours, during which time complex 5 dissolves. The addition of THF to the solution causes the formation of a precipitate, which is recovered by centrifugation. 15 mg (15 µmol) of complex 19 are obtained (corresponding to a yield of 68%) in the form of a white powder.

EXAMPLE 16

Preparation of Complex 20 of Formula

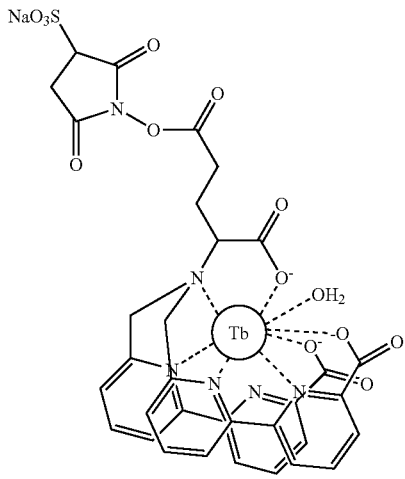

45 mg (55 µmol) of complex 8 are suspended in 10 mL of DMSO in a 50 mL round-bottomed flask. To this solution are added 14 mg (60 µmol) of the monosodium salt of N-hydroxy-succinimide-3-sulfonic acid hydrate and 12 mg (63 µmol) of ethyl-N,N-dimethyl-3-aminopropylcarbodiimide hydrochloride (EDCI.HCl). The solution is stirred at room temperature for 92 hours, during which time complex 8 dissolves. The addition of THF to the solution causes the formation of a precipitate, which is recovered by centrifugation. 45 mg (44 µmol) of complex 20 are obtained (corresponding to a yield of 81%) in the form of a yellow powder, the characteristics of which are as follows:

Analyses calculated for $C_{33}H_{24}N_6NaO_{13}STb.5H_2O$: C 38.99, H 3.37, N 8.27. Found: C 39.20, H 3.56, N 8.39.

$FAB^+/MS$: 682.2 ($[20-H_2O-C_5H_3NNaO_7S]^+$, 95%), 727.2 ($[20-H_2O-C_4H_3NNaO_5S+H]^+$, 55%).

EXAMPLE 17

Preparation of Complex 21 of Formula

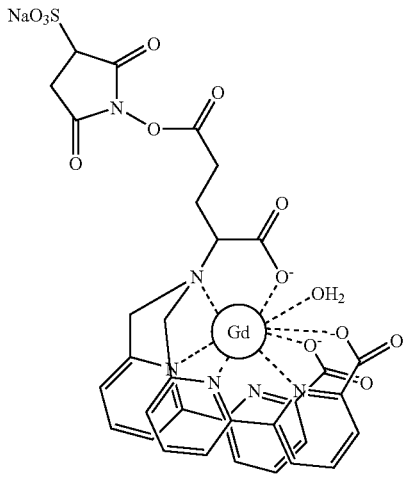

19 mg (24 μmol) of complex 10 are suspended in 5 mL of DMSO in a 10 mL round-bottomed flask. To this solution are added 7 mg (30 μmol) of the monosodium salt of N-hydroxy-succinimide-3-sulfonic acid hydrate and 5 mg (26 μmol) of ethyl-N,N-dimethyl-3-aminopropylcarbodiimide hydrochloride (EDCI.HCl). The solution is stirred at room temperature for 24 hours, during which time complex 10 dissolves. The addition of THF to the solution causes the formation of a precipitate, which is recovered by centrifugation. 19 mg (19 μmol) of complex 21 are obtained (corresponding to a yield of 80%) in the form of a yellow powder, the characteristics of which are as follows:

$FAB^+/MS$: 681.2 ($[21-H_2O-C_5H_3NNaO_7S]^+$, 100%), 726.3 ($[21-H_2O-C_4H_3NNaO_5S+H]^+$, 40%).

EXAMPLE 18

Preparation of Compound 25

Compound 25 is obtained in four steps according to the following scheme:

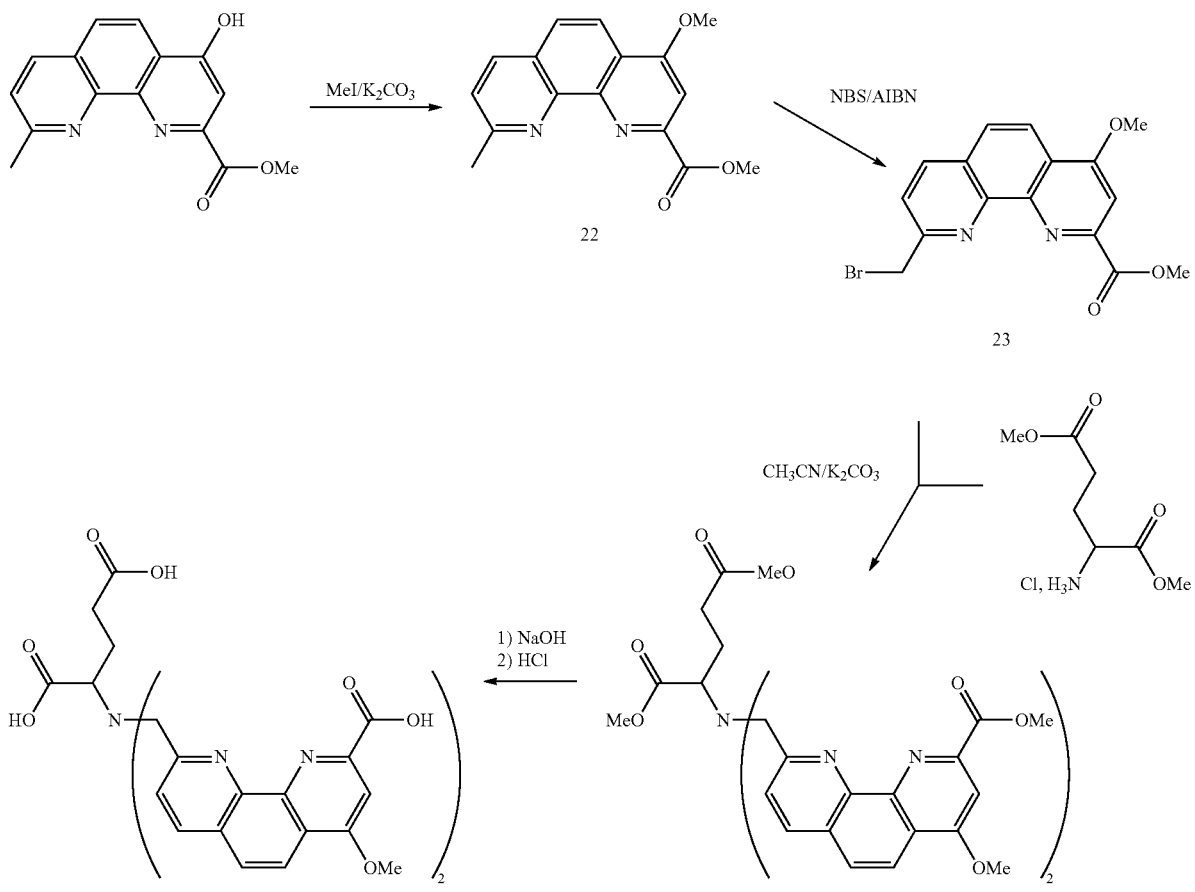

Preparation of Compound 22

2.04 g (7.6 mmol) of 7-hydroxy-9-carbomethoxy-2-methylphenanthroline (obtained according to Heindel, N. et al, J. Heterocycl. Chem. 1968, 5, 869), 2.11 g (15.2 mmol) of $K_2CO_3$ and 950 μL (15.3 mmol) of methyl iodide are introduced into 60 ml of acetonitrile freshly distilled over $P_2O_5$, in a Schlenk tube under an argon atmosphere. The solution is heated at 80° C. for 19 hours. The solution is evaporated to dryness and the residue is dissolved in 100 mL of $CH_2Cl_2$ and 15 mL of water. The aqueous phase is extracted with 4 portions of 15 mL of $CH_2Cl_2$ and the combined organic phases are dried over $MgSO_4$, filtered and then evaporated to dryness. The residue is purified by chromatography on alumina (φ=5 cm, h=12 cm) with a $CH_2Cl_2$/MeOH mixture (99/1) as eluent. 2.05 g (7.3 mmol) of compound 22 are obtained (corresponding to a yield of 95%) in the form of a yellow powder having the following characteristics:

$R_f$=0.54, $Al_2O_3$, $CH_2Cl_2$/MeOH (98/2).

$^1$H-NMR (CDCl$_3$, 200 MHz): δ 2.91 (s, 3H), 4.06 (s, 3H), 4.12 (s, 3H), 7.47 (d, 1H, $^3$J=8.5 Hz), 7.77 (d, 1H, $^3$J=9.0 Hz), 7.83 (s, 1H), 8.08 (d, 1H, $^3$J=7.5 Hz), 8.12 (d, 1H, $^3$J=9.0 Hz).

$^{13}$C-NMR (CDCl$_3$, 50 MHz): δ 25.8, 52.8, 56.2, 102.9, 118.7, 122.2, 123.9, 126.9, 127.4, 136.0, 145.2, 146.1, 148.6, 160.1, 163.2, 166.5.

Analyses calculated for $C_{16}H_{14}N_2O_3$: C 68.07, H 5.00, N 9.92.

Found: C 67.92, H 4.93, N 9.78.

FAB$^+$/MS: 283.2 ([22+H]$^+$, 100%).

Preparation of Compound 23

1 g (3.5 mmol) of compound 22, 630 mg (3.5 mmol) of N-bromosuccinimide and 30 mg (0.2 mmol) of azobis-isobutyronitrile (AIBN) are introduced into 10 mL of benzene in a 250 mL round-bottomed flask. The solution is irradiated for 30 minutes with a standard 100 W halogen lamp. The solvent is evaporated off under reduced pressure and the residue is purified by chromatography on alumina containing 10% water with a mixture of $CH_2Cl_2$/hexane (50/50) as eluent. 468 mg (1.3 mmol) of compound 23 are obtained (corresponding to a yield of 37%) in the form of a gray powder having the following characteristics:

$R_f$=0.71, $Al_2O_3$, $CH_2Cl_2$/MeOH (98/2).

$^1$H-NMR (CDCl$_3$, 200 MHz): δ 4.06 (s, 3H), 4.12 (s, 3H), 4.93 (s, 2H), 7.77 (d, 1H, $^3$J=9.0 Hz), 7.83 (s, 1H), 7.87 (d, 1H, $^3$J=8.5 Hz), 8.17 (d, 1H, $^3$J=9.0 Hz), 8.21 (d, 1H, $^3$J=8.5 Hz).

$^{13}$C-NMR (CDCl$_3$, 50 MHz): δ 34.6, 53.0, 56.3, 103.3, 120.2, 122.4, 123.7, 127.0, 128.1, 137.1, 144.5, 145.9, 148.9, 157.6, 163.3, 166.2.

Analyses calculated for $C_{16}H_{13}BrN_2O_3$: C 53.21, H 3.63, N 7.76.

Found: C 52.94, H 3.26, N 7.51.

FAB$^+$/ MS: 281.2 ([23-Br]$^+$, 30%), 361.2 (100%), 363.2 (100%), [23+H]$^+$.

Preparation of Compound 24

96 mg (0.45 mmol) of dimethyl DL-glutamate hydrochloride and 250 mg (1.81 mmol) of $K_2CO_3$ are introduced into 15 mL of acetonitrile freshly distilled over $P_2O_5$, in a Schlenk tube under an argon atmosphere. The solution is heated at 80° C. for 10 minutes. 360 g (1 mmol) of compound 23 are added and the mixture is heated for 18 hours at 80° C. A further portion of compound 23 (52 mg, 0.14 mmol) is added and the mixture is heated for 24 hours at 80° C. The solution is evaporated to dryness and the residue is dissolved in 30 ml of $CH_2Cl_2$ and 10 mL of water. The aqueous phase is extracted with 4 portions of 30 mL of $CH_2Cl_2$ and the combined organic phases are dried over $MgSO_4$, filtered and then evaporated to dryness. The residue is purified by chromatography on alumina containing 10% water with a mixture of $CH_2Cl_2$/MeOH (100/0 to 99.3/0.7) as eluent. 46 mg (0.06 mmol) of compound 24 are obtained (corresponding to a yield of 37%), which product has the following characteristics:

$R_f$=0.16, $Al_2O_3$, $CH_2Cl_2$/MeOH (98/2).

$^1$H-NMR (CDCl$_3$, 200 MHz): δ 2.17-2.28 (m, 2H), 2.61 (t, 2H, $^3$J=7.5 Hz), 3.44 (s, 3H), 3.71 (t, 1H, $^3$J=7.5 Hz), 3.83 (s, 3H), 4.06-4.19 (m, 12H), 4.45-4.70 (m, 4H), 7.82 (d, 2H, $^3$J=9.0 Hz), 7.86 (s, 2H), 8.13 (d, 2H, $^3$J=8.0 Hz), 8.18 (d, 2H, $^3$J=9.0 Hz), 8.24 (d, 2H, $^3$J=8.5 Hz).

Preparation of Compound 25.3HCl 46 mg (0.06 mmol) of 24 and 10 mg (0.25 mmol) of NaOH are dissolved in a mixture of 9 mL of MeOH and 3 mL of water in a 50 mL round-bottomed flask. The mixture is heated at 75° C. for 21 hours. The solvents are evaporated off under reduced pressure, the solid is dissolved in 5 mL of water and the solution obtained is filtered through Celite. The medium is acidified with dilute hydrochloric acid solution and the solution is evaporated to dryness. The residue is washed with 2 portions of 2 mL of water. 19 mg (0.02 mmol) of 25.3HCl hydrochloride are obtained (corresponding to a yield of 39%) in the form of an orange-yellow powder, the characteristics of which are as follows:

$^1$H-NMR (CD$_3$OD, 200 MHz): δ 2.38-2.52 (m, 2H), 2.84 (t, 2H, $^3$J=7.0 Hz), 4.17 (t, 1H, $^3$J=7.5 Hz), 4.35 (s, 6H), 4.81-4.85 (m, 4H), 7.87 (d, 2H, $^3$J=9.5 Hz), 7.89 (s, 2H), 8.16 (d, 2H, $^3$J=9.0 Hz), 8.18 (d, 2H, $^3$J=8.5 Hz), 8.65 (d, 2H, $^3$J=9.0 Hz).

EXAMPLE 19

Preparation of Compound 26 of Formula [Eu.(25-4H).H$_2$O]Na

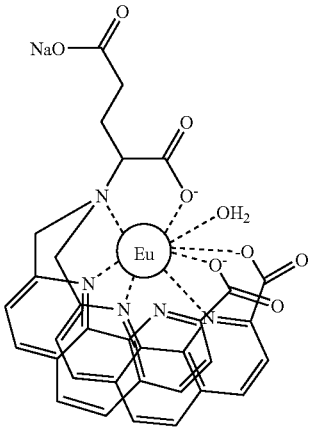

19 mg of 25.3HCl (24 μmol) are dissolved in a mixture of 15 mL of MeOH and 15 mL of water in a 50 mL round-bottomed flask. To this solution are added 10 mg (27 μmol) of EuCl$_3$.6H$_2$O dissolved in 2.5 mL of MeOH and 2.5 mL of water. The solution is heated at 70° C. for one hour. After cooling, the pH of the solution is raised to 7.0 with a 0.5% solution of NaOH in water. The solution is concentrated on a rotary evaporator until slight cloudiness appears, and THF is then added until a precipitate forms. The yellow solid is isolated by centrifugation and then dried under vacuum to give 7 mg (8 μmol) of compound 26 (corresponding to a yield of 33%), the characteristics of which are as follows:

FAB$^-$/MS: 791.2 (30%), 828.2 ([26-H$_2$O-Na)]$^-$, 50%).

EXAMPLE 20

Marking of an Anti-digoxigenine Antibody with Complex 9 and Characterization by Mass Spectrometry 0.5 mg of complex 9 is added to a solution of anti-digoxigenine antibody containing 1.0 mg of antibody dissolved in 500 μL of buffer solution (50 mM borate buffer, pH=7.0), corresponding to a 9/antibody ratio of 30:1. The solution is stirred at room temperature for 24 hours, and the marked antibody is then purified according to the procedure described in Example 5 and stored at 4° C.

Characterization by MALDI-TOF mass spectrometry is performed according to the procedure described in Example 5, leading to a mass of 49 220 Da for the marked antibody (47 880 Da for the free antibody), i.e. a degree of grafting of 2.5.

The invention claimed is:

1. A process for preparing a lanthanide complex comprising reacting a compound of formula (I)

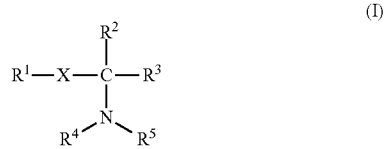

with a compound comprising a lanthanide cation,
wherein in the compound of formula (I):
$R^1$ is a functional group capable of reacting with the functions present on proteins, antibodies or on mineral or organic materials;
X represents a single bond or a hydrocarbon-based chain consisting of at least one group chosen from alkylene groups and alkenylene groups optionally comprising at least one hetero atom, and from arylene groups;
$R^2$ is a group $A^2$ that is anionic at neutral pH or an alkylene or alkenylene group containing from 1 to 4 carbon atoms and bearing at least one such group $A^2$, said alkylene or alkenylene group optionally comprising at least one hetero atom in the chain;
$R^3$ represents H or an alkylene or alkenylene group containing from 1 to 5 carbon atoms and optionally containing at least one hetero atom in the chain, said group optionally bearing at least one group $A^3$ that is anionic at neutral pH;
$R^4$ is chosen from the groups corresponding to the formula $-(C)_n-C-Z^1-C-C-Z^2-C-A^4$ in which n is equal to 1 or 2, $Z^1$ and $Z^2$ represent, independently of each other, a hetero atom chosen from O and N, at least one being a nitrogen atom forming part of an aromatic heterocycle with the two carbon atoms surrounding it, and $A^4$ is a group that is anionic at neutral pH, in which the atom bearing the anionic charge is in the γ position relative to $Z^2$; and
$R^5$ is chosen from the groups defined for $R^4$ or from groups corresponding to the formula $-C-C-E^1-C-C-E^2-C-A^5$ in which $E^1$ and $E^2$ represent, independently of each other, a hetero atom chosen from O and N, and $A^5$ is a group that is anionic at neutral pH, in which the atom bearing the anionic charge is in the γ position relative to $E^2$.

2. The process as claimed in claim 1, wherein the compound comprising a lanthanide cation is selected from the group consisting of lanthanide halide hydrates, lanthanide nitrate hydrates, lanthanide carbonates and lanthanide triflates.

3. The process as claimed in claim 1, wherein the reaction is performed in solution in a solvent selected from the group consisting of water, methanol, ethanol and acetonitrile.

4. The process as claimed in claim 1, wherein compound of formula (I) is reacted with the lanthanide ion precursor in a mixture of methanol and water at a pH ranging from 3 to 5, for a time of between 10 minutes and 24 hours, at a temperature of between 25° C. and 80° C., and the pH of the solution is then adjusted to 7.0 and the methanol is evaporated off.

5. A complex obtained via a process as claimed in claim 1, wherein the complex comprises a lanthanide ion Ln complexed with a ligand corresponding to a compound of formula (I).

6. The complex as claimed in claim 5, wherein the lanthanide ion is selected from the group consisting of from europium, terbium, samarium, dysprosium, erbium, ytterbium, neodymium and gadolinium ions.

7. The complex as claimed in claim 5, wherein the substituent $R^4$ of the compound of formula (I) is $-C-C-Z^1-C-C-Z^2-C-A^4$, the 3 chelate rings being formed between the lanthanide cation and, respectively:
the N atom bearing $R^4$ and $R^5$, $Z^1$ and the carbon atoms that separate them;
$Z^1$, $Z^2$ and the two carbon atoms that separate them;
the end segment $Z^2-C-A^4$.

8. The complex as claimed in claim 7, wherein the substituent $R^5$ is of the same type as the substituent $R^4$.

9. The complex as claimed in claim 7, wherein the substituent $R^5$ is of the type $-C-C-E^1-C-C-E^2-C-A^5$, three 5-membered chelate rings being formed between the lanthanide cation and, respectively:
the N atom bearing $R^4$ and $R^5$, $E^1$ and the two carbon atoms that separate them;
$E^1$, $E^2$ and the two carbon atoms that separate them;
the end segment $E^2-C-A^5$.

10. A process for the quantitative or qualitative analysis of a compound, comprising: covalently bonding to said compound a marker consisting of a complex as claimed in claim 8, and detecting or quantifying the presence of the marked compound by means of the luminescence properties of the marker.

11. The process as claimed in claim 10, wherein the complex is a europium, terbium, samarium or dysprosium complex.

12. The process as claimed in claim 10, wherein the substituent $R^1$ of the complex is selected from amino, thio and carboxyl groups or from maleimido, N-succinimidyl ester and isothiocyano groups.

13. A relaxation agent for nuclear magnetic resonance, consisting of a complex as claimed in claim 5.

14. The relaxation agent as claimed in claim 13, wherein the complex is a gadolinium, europium or dysprosium complex.

15. The relaxation agent as claimed in claim 13, wherein the complex is a complex in which the substituent $R^1$ is selected from amino, thio and carboxyl groups or from maleimido, N-succinimidyl ester and isothiocyano groups.

* * * * *